US007417176B2

(12) United States Patent
Lardizabal et al.

(10) Patent No.: US 7,417,176 B2
(45) Date of Patent: Aug. 26, 2008

(54) DIACYLGLYCEROL ACYLTRANSFERASE NUCLEIC ACID SEQUENCES AND ASSOCIATED PRODUCTS

(75) Inventors: Kathryn D. Lardizabal, Woodland, CA (US); Kristen A. Bennett, Davis, CA (US); Nicholas W. Wagner, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 472 days.

(21) Appl. No.: 10/631,581

(22) Filed: Jul. 31, 2003

(65) Prior Publication Data
US 2004/0107459 A1 Jun. 3, 2004

Related U.S. Application Data

(60) Provisional application No. 60/399,427, filed on Jul. 31, 2002.

(51) Int. Cl.
*C12N 15/82* (2006.01)
*C12N 15/87* (2006.01)

(52) U.S. Cl. .................... 800/281; 800/23.74; 800/288; 800/295; 435/320.1

(58) Field of Classification Search ...................... None
See application file for complete search history.

(56) References Cited

U.S. PATENT DOCUMENTS

| | | | |
|---|---|---|---|
| 5,880,334 | A | 3/1999 | Suzuki et al. |
| 6,051,755 | A | 4/2000 | Zou et al. |
| 6,100,077 | A | 8/2000 | Sturley et al. |
| 6,344,548 | B1 | 2/2002 | Farese et al. |
| 6,444,876 | B1 | 9/2002 | Lassner et al. |
| 6,791,008 | B1 * | 9/2004 | Banas et al. ................. 800/281 |
| 2002/0119138 | A1 | 8/2002 | Cases et al. ................. 424/94.5 |

FOREIGN PATENT DOCUMENTS

| | | |
|---|---|---|
| WO | WO 98/55631 A | 12/1998 |
| WO | WO 99/67268 | 12/1999 |
| WO | WO 00/01713 A2 | 1/2000 |
| WO | WO 00/32793 | 6/2000 |
| WO | WO 00/66749 | 11/2000 |
| WO | WO 02/068595 | 9/2002 |
| WO | WO2006069610 | 7/2006 |

OTHER PUBLICATIONS

Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Fourgoux-Nicol et al 1999, Plant Molecular Biology 40:857-872.*
SEQ ID No. 84, 2000, WO 2000/01713.*
Search result for AAZ60407 (3 pages in total).*
U.S. Appl. No. 10/121,857, filed Apr. 15, 2002, Lardizabal et al.

Coleman et al.; "Physiological and Nutritional Regulation of Enzymes of Triacylglycerol Synthesis"; Annu. Rev. Nutr.; 20:77-103 (2000).
Daum et al.; "Biochemistry, Cell Biology and Molecular Biology of Lipids of *Saccharomyces cerevisiae*"; Yeast; 14(16):1471-1510 (1998).
Harwood et al.; "Recent Advances in the Biosynthesis of Plant Fatty Acids"; Biochem. Biophysics. Acta; 1301:7-56 (1996).
Kamiska et al.; "Activation of Detergent-Solubilized Diacylglycerol Acyltransferase by Anionic Phospholipids"; J. Biochem.; 119:520-523 (1996).
Kamiska et al.; "Characterization of the Diacylglycerol Acyltransferase Activity in the Membrane Fraction From a Fungus"; Lipids; 28:583-587 (1993).
International Preliminary Examination Report PCT/US03/24822.
PCT Written Opinion PCT/US03/24822.
International Search Report PCT/US03/24822.
Response to Written Opinion PCT/US03/24822.
International Preliminary Examination Report PCT/US99/15243.
PCT Written Opinion PCT/US99/15243.
International Search Report PCT/US99/15243.
Anderson et al., "Purification of diacylglycerol:acyltransferase from rat liver to near homogeneity", Journal of Lipid Research, U.S., Bethesda, MD, No. 35:535-545 (1994), (XP002079127), Abstract.
Cases, S. et al., "Identification of a gene encoding an acyl CoA: diacylclycerol acyltransferase, a key enzyme in triacylglycerol syntheses", Proceedings of the National Academy of Sciences of USA, US, National Academy of Science, Washington, vol. 95, No. 22:13018-13023 (1998), (XP002122745), Abstract.
Kwanyen et al., "Isolation and purification of diacylglycerol acyltransferase from germinating soybean cotyledons", BBA-Lipids and Lipid Metabolism, NL, Elsevier Science BV. Amsterdam, No. 877:238-245 (1986), (XP002079128).
Newman et al., "*Arabidopsis thaliana* cDNA clone 16101T7", EMBL Accession No. AT83514 (XP002146441), Abstract.
Marra et al., "*Mus musculus* cDNA clone Image:1276709", EMBL Accession No. AA880703 (XP002146443), Abstract.
Hillier et al., "*Homo sapiens* cDNA clone Image:488805", EMBL Accession No. HS84166 (XP002146442), Abstract.
Marra et al., "*Mus musculus* cDNA clone Image:1243243", EMBL Accession No. AA822348 (XP002146444), Abstract.
Marra et al., "*Mus musculus* cDNA clone Image:1277098", EMBL Accession No. AA880955 (XP002146445), Abstract.
Wilson et al., "*Caenorhabditis elegans* cosmid K07B1", (XP002146446), EMBL Accession No. CEAF3384, Abstract.
Little et al., "Solubilization and characterization of diacylglycerol acyltmasferase from microspore-drived cultures of oilseed rape", Biochemical Journal, GB, Portland Press, London, No. 304:951-958 (1994), (XP002079126).

(Continued)

*Primary Examiner*—Ashwin Mehta
*Assistant Examiner*—Li Zheng
(74) *Attorney, Agent, or Firm*—Sonnenschein Nath & Rosenthal LLP

(57) ABSTRACT

The present invention is directed to polypeptides and nucleic acid sequences related thereto, and methods to purify, obtain, and use such molecules in genetic engineering applications. More specifically, the present invention relates to polypeptides associated with the production of triacylglycerols in plants and fungi.

23 Claims, 11 Drawing Sheets

OTHER PUBLICATIONS

Boyer et al., "*S. cerevisiae* chromosome XV reading frame ORF YOR245c", EMBL Accession No. SCYOR245C (XP002146447), Abstract.

Bell et al., "Enzymes of Glycerolipid Synthesis in Eukaryotes," Ann. Rev. Biochem., 49:459-487 (1980).

Brindley, D.N., "Metabolism of triacylglycerols", in Biochemistry of Lipids, Lipoproteins and Membranes, eds. Vance, D.E. & Vance J.E. (Elsevier, Amsterdam), pp. 171-203 (1991).

Nishizuka, Y., "Intracellular signaling by hydrolysis of phospholipids and activation of protein kinase C", Science, 258:607-614 (1992).

Hobbs et al., "Cloning of a cDNA encoding diacylglycerol acyltransferase from *Arabidopsis thaliana* and its functional expression", FEBS Letters, 452:145-149 (1999).

Katavic et al., "Alteration of seed fatty acid composition by an ethyl methanesulfonate-induced mutation in *Arabidopsis thaliana* affecting diacylglycerol acyltransferase activity", Plant Physiol., 108:399-409 (1995).

Zou et al., "The *Arabidopsis thaliana* TAG1 mutant has a mutation in a diacylglycerol acyltransferase gene", The Plant Journal, 19(6):645-653 (1999).

Routaboul et al., "The TAG1 locus of *Arabidopsis* encodes for a diacylglycerol acyltransferase", Plant Physiol. Biochem., 37(11):831-840 (1999).

Kamisaka et al., "Purification and characterization of diacylglycerol acyltransferase from the lipid body fraction of an oleaginous fungus", J. Biochem. 121:1107-1114 (1997) (XP-002079124).

Laemmli, U.K., "Cleavage of structural proteins during the assembly of the head of bacteriophage T4", Nature, 277:680-685 (1970).

Delepelaire et al., "Lithium dodecyl sulfate/polyacrylamide gel electrophoresis of thylakoid membranes at 4° C: characterization of two additional chlorophyll a-protein complexes", Proceedings of the National Academy of Sciences of USA, 76:111-115 (1979).

Blum et al., "Improved silver staining of plant proteins, RNA and DNA in polyacrylamide gels", Electrophoresis, 8:93-99 (1987).

Jones et al., "Palmitoyl-Acyl carrier protein (ACP) thioesterase and the evolutionary origin of plant Acyl-ACP thioesterases", The Plant Cell, 7:359-371 (1995).

Neuwald, F., "Barth syndrome may be due to an acyltransferase deficiency", Current Biology, 7(8):465-466 (1997).

Lewin et al., "Analysis of amino acid motifs diagnostic for the sn-Gycerol-3-phosphate acyltransferase reaction", Biochemistry, 38:5764-5771 (1999).

Smith et al., "Obesity resistance and multiple mechanisms of triglyceride synthesis in mice lacking Dgat", Nature Genetics, 25:87-90 (2000).

Stobart et al., "Triacylglycerols are synthesized and utilized by transacylation reactions in microsomal preparations of developing safflower (*Carthamus tictorius* L.) seeds", Planta, 203:58-66 (1997).

Dahlqvist et al., "Selective channelling of unusual fatty acids into triacylglycerols," in Advances in Plant Lipid Research, Eds. Sanches, J.I. et al. (Universidad de Sevilla, Seville, Spain), pp. 211-214 (1998).

Dahlqvist et al., "Phospholipid:diacylglycerol acyltransferase: An enzyme that catalyzes the acyl-CoA-independent formation of triacylglycerol in yeast and plants", Proceedings of the National Academy of Sciences of USA, 97(12):6487-6492 (2000).

Oelkers et al., "A lecitihin cholesterol acyltransferase-like gene mediates diacylglycerol esterification in yeast", J. Biol. Chem., 275(21):15609-15612 (2000).

Bouvier-Nave et al., "Expression in yeast and tobacco of plant cDNAs encoding acyl CoA:diacylglycerol acyltransferase", Eur. J. Biochem., 267:85-96 (2000).

Knutzon et al., "Modification of Brassica seed oil by antisense expression of a stearoyl-acyl carrier protein desaturase gene", Proc. Natl. Acad. Sci. USA,. 89:2624-2628 (1992).

Voelker et al., "Fatty acid biosynthesis redirected to medium chains in transgenic oilseed plants", Science, 257:72-74 (1992).

Metz et al., "Purification of a jojoba embryo fatty acyl-coenzyme a reductase and expression of its cDNA in high erucic acid rapeseed", Plant Physiol., 122:635-644 (2000).

Lardizabal et al., "Purification of a jojoba embryo wax synthase, cloning of its cDNA, and production of high levels of wax in seeds of transgenic *Arabidopsis*", Plant Physiology, 122:645-655 (2000).

Roesler et al., "Targeting of the *Arabidopsis* homomeric acetyl-coenzyme A carboxylase to plastids of rapeseeds", Plant Physiol., 113:75-81 (1997).

Bradford, M., "A Rapid and sensitive method for the quantitation of microgram quantities of protein utilizing the principle of protein-dye binding", Anal. Biochem., 72:248-254 (1976).

Database Geneseq, "*Arabidopsis thaliana* DNA fragment SEQ ID No. 3835," Database accession No. AAC33653, 2000.

Sandager et al.: "Storage lipid synthesis is non-essential in yeast," *Journal of Biological Chemistry*, 227:6478-6482, 2002.

Wilson et al,: "Recent developments in the molecular biochemistry and genetics of diacyglycerol acyltransferase from soybean," In: Seed Oils for the Future, Aocs Press, Champaign, IL, pp. 116-135, 1992.

Cases et al., "Cloning of DGAT2, a second mammalian diacylglycerol acyltransferase, and related family members," *J. Biol Chem.*, 276(42):38870-38876, 2001.

Goodrich-Tanrikulu et al., "Changes in fatty acid composition of *Neurospora crassa* accompany sexual development and ascospore germination," *Microbiology*, 144(7):1713-1720, 1998.

Lardizabal et al., "DGAT2 is a new diacylglycerol acyltransferase gene family. Purification, cloning, and expression in insect cells of two polypeptides from *Mortierella ramanniana* with diacylglycerol acyltransferase activity," *J. Biol. Chem.*, 276(42):38862-38869, 2001.

* cited by examiner

| Gene | SEQ ID NO | Primer sequences |
|---|---|---|
| NcDGAT2 | 7 | 5'GGATCCCGGTCCGAAGCGCATGGAGCGGGATAGAGCCAACG 3' |
|  | 8 | 5'AAGCTTGGTACCCTATTTCAGTATCTGCATTTCCTCAATCCG 3' |
| NcDGAT2 | 9 | 5'AAAAGCGGCCGCATGGAGCGGGATAGAGCCAACG 3' |
|  | 10 | 5' AAAACCTGCAGGCTATTTCAGTATCTGCATTTC 3' |

Figure 12a

```
MrDGAT    Q GA-SI VETISFG NEL YEQIESNENSK HR  KKIQHA  FIM LEHGR VEN DFC LIE HRFE YTI
MrDGAT    RN GA-SI VE IFSFG NDI YEQYDNKKGSLIWRY  KWFQKIT FIV LAHARG IEN  NA  F  ERH IVTV
NcDGA     R  GA-DIVE VLA FG NDI YDQVSPKSHPYTHRI  MFVLRTE F L FTHGR IEN DV  IM YRFE LNIV
CaDGA     EI GNVAI VE FA FG EAD VYRLVQPSTSMMYKF  KWMKGIFT N  F LESAR VE IYD  II ERNE INIC
ScDGA     QI GNINI VE FA FG H VDQMNVLSTKDSVEGKM  LMEKENFG MI IF EYAR IEN DF  HI ERAE INVV

MrDGAT    VC KPI PVP----------------------SIKYGQTK---DEIIRELHDSY
MrDGAT    VC KPI AVP----------------------LLAEGETEPSEEQMHQVQAQY
NcDGA     VC KPI RVT----------------------KRAESDLETSE---IDQLHGIY
CaDGA     VC KPI YTIPAGALQEYKQQHPEEFTEEETKPPMKKSGSFTDIFKMNGETPKVSTIKTKIPPALIDKYHKLY
ScDGA     VG RPI YVE--------------------------KKI------TNPPDDVVNHFHDLY

MrDGAT    MHAVQDLYDRYKDIYAKDRVKEEEFVE.
MrDGAT    IESLQAIYDKYKDIYAKDRIKDMTMIA.
NcDGA     VKELEKMWERYKDGFAPERIEEMQILK.
CaDGA     VDELRNVYEENKHKFGYGDV-EFSIVE.
ScDGA     IAELKRLYENREKYGVPDA-EEKIVG.
```

DIACYLGLYCEROL ACYLTRANSFERASE NUCLEIC ACID SEQUENCES AND ASSOCIATED PRODUCTS

This application claims the benefit of U.S. Provisional Application 60/399,427 filed Jul. 31, 2002, which is incorporated herein by reference.

The present invention is directed to polypeptides and nucleic acid sequences related thereto, and methods to purify, obtain, and use such molecules in genetic engineering applications. More specifically, the present invention relates to polypeptides associated with the production of triacylglycerols in plants, fungi, and mammals.

Diacylglycerol acyltransferase (referred to hereinafter as DGAT) is an integral membrane protein that catalyzes the final enzymatic step in the production of triacylglycerols in plants, fungi, and mammals. DGAT has generally been described in Harwood, *Biochem. Biophysics. Acta*, 13017-13056 (1996); Daum et al., *Yeast*, 16:1471-1510 (1998); and Coleman et al., *Annu. Rev. Nutr.*, 20:77-103 (2000). This enzyme is responsible for transferring an acyl group from acyl-coenzyme-A to the sn-3 position of 1,2-diacylglycerol (DAG) to form triacylglycerol (TAG). In plants and fungi, DGAT is associated with the membrane and lipid body fractions, particularly in oilseeds, where it contributes to the storage of carbon used as energy reserves. TAG is believed to be an important chemical for storage of energy in cells. DGAT is known to regulate TAG structure and direct TAG synthesis. Furthermore, it is known that the DGAT reaction is specific for oil synthesis.

In plants, TAG is the primary component of vegetable oil that is used by the seed as a stored form of energy to be used during seed germination. Higher plants are believed to synthesize oils via a similar metabolic pathway commonly referred to as the Kennedy pathway (Kennedy et al., *J. Biol. Chem.*, 222:193 (1956); Finnlayson et al., *Arch. Biochem. Biophys.*, 199:179-185 (1980)). Fatty acids are made in plastids from acetyl-CoA through a series of reactions catalyzed by enzymes known collectively as Fatty Acid Synthase (FAS). The fatty acids produced in plastids are exported to the cytosolic compartment of the cell, and are esterified to coenzyme A. These acyl-CoAs are the substrates for glycerolipid synthesis on the endoplasmic reticulum (ER). Glycerolipid synthesis itself is a series of reactions leading first to phosphatidic acid (PA) and DAG. Either of these metabolic intermediates may be directed to membrane phospholipids such as phosphatidylglycerol (PG), phosphatidylethanolamine (PE), or phosphatidylcholine (PC), or they may be directed on to form neutral triacylglycerol (TAG).

DAG is synthesized from glycerol-3-phosphate and fatty acyl-CoAs in two steps catalyzed sequentially by glycerol-3-phosphate acyltransferase (G3PAT), and lysophosphatidic acid acyltransferase (LPAAT) to make PA, and then an additional hydrolytic step catalyzed by phosphatidic acid phosphatase (PAP) to make DAG. In most cells, DAG is used to make membrane phospholipids, the first step being the synthesis of PC catalyzed by CTP-phosphocholine cytidylyltransferase. In cells producing storage oils, DAG is acylated with a third fatty acid in a reaction catalyzed by DGAT.

Two different families of DGAT proteins have been identified. The first family of DGAT proteins (referred to herein after as DGAT1) is related to the acyl-coenzyme A:cholesterol acyltransferase (ACAT) and has been described in the literature (see, e.g. U.S. Pat. Nos. 6,100,077 and 6,344,548). A second family of DGAT proteins (referred to hereinafter as DGAT2), unrelated to the previously identified family of DGAT1 proteins, is described in the present invention. This family of DGAT2 proteins is also described in U.S. Pat. No. 6,822,141.

Obtaining nucleic acid sequences capable of producing a phenotypic result in the incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful tissue sources for nucleic acid sequences of such enzyme targets capable of modifying oil structure and quantity are needed. Ideally, an enzyme target will be amenable to one or more applications alone or in combination with other nucleic acid sequences relating to increased or decreased oil production, TAG structure, the ratio of saturated to unsaturated fatty acids in the fatty acid pool, and/or to other novel oil compositions as a result of the modifications to the fatty acid pool.

SUMMARY OF THE INVENTION

The present invention provides genetic tools that answers the need of both altering the composition of oils produced in a plant as well as the percentage content thereof relative to other components of a seed, including, for example, the meal content thereof. The present invention includes diacylglycerol acyltransferase (DGAT) polypeptides and polynucleotides encoding these polypeptides. The polypeptides and polynucleotides of the present invention include those derived from plant and fungal sources, including, for example, *Mortierella ramanniana*, *Saccharomyces cerevisiae*, and *Neurospora crassa*.

The present invention further relates to polynucleotides that encode the DGAT proteins, and polynucleotides that include partial or complete DGAT encoding sequences. The present invention also provides polynucleotides that encode the DGAT2 proteins, and polynucleotides that include partial or complete DGAT2 encoding sequences.

The present invention also provides recombinant DNA constructs that can be used for transcription and expression of DGAT2, including constructs that are capable of expressing DGAT2 in plant, and insect host cells.

The present invention also includes an isolated nucleic acid molecule comprising a nucleic acid sequence that encodes a polypeptide molecule comprising a polypeptide sequence selected from the group consisting of SEQ ID NOs: 14, 18, 20, 22, 24, 26, and 28. Preferred such isolated nucleic acid molecules include, for example, SEQ ID NOs: 11, 12, 13, 16, 17, 19, 21, 23, 25, and 27.

The present invention includes an isolated nucleic acid molecule comprising a nucleic acid sequence that encodes a polypeptide having homology to a diacylglycerol acyltransferase, wherein the nucleic acid molecule is selected from the group consisting of SEQ ID NOs: 11, 12, 13, 16, 17, 19, 21, 23, 25, and 27.

The present invention also includes DNA constructs comprising an expression cassette comprising a heterologous promoter that functions in a plant cell operably linked to a nucleic acid molecule that encodes a polypeptide molecule comprising a polypeptide sequence selected from the group consisting of SEQ ID NOs: 14, 18, 20, 22, and 24. In certain embodiments the DNA construct further comprises a second expression cassette, wherein said second expression cassette comprises a second heterologous promoter that functions in a plant cell operably linked to a nucleic acid that encodes a polypeptide for a diacylglycerol acyltransferase. Preferably, the second heterologous promoter is different or the same from the heterologous promoter used initially; more preferably, the two heterologous promoters are different.

The present invention also includes a DNA construct comprising an expression cassette comprising a heterologous promoter that functions in a plant cell operably linked to a nucleic acid molecule that encodes a polypeptide having homology to a diacylglycerol acyltransferase, wherein the nucleic acid molecule is selected from the group consisting of SEQ ID NOs: 11, 12, 13, 16, 17, 19, 21, and 23. In certain embodiments the DNA construct further comprises a second expression cassette wherein said second expression cassette comprises a second heterologous promoter that functions in a plant cell operably linked to a nucleic acid that encodes a polypeptide for a diacylglycerol acyltransferase. Preferably, the second heterologous promoter is different or the same from the heterologous promoter used initially; more preferably, the two heterologous promoters are different.

The present invention also includes a plant or seed comprising the DNA construct comprised of expression cassette comprising a heterologous promoter that functions in a plant cell operably linked to a nucleic acid molecule that encodes a polypeptide having homology to a diacylglycerol acyltransferase, wherein the nucleic acid molecule is selected from the group consisting of SEQ ID NOs: 11, 12, 13, 16, 17, 19, 21, and 23. Preferably, the plant or seed is one or more of maize, soybean, canola, oil seed rape, cotton, sesame, flax, peanut, sunflower, safflower, olive, and oil palm.

The present invention also includes a plant or seed comprising the DNA construct comprised of an expression cassette comprising a heterologous promoter that functions in a plant cell operably linked to a nucleic acid molecule that encodes a polypeptide molecule comprising a polypeptide sequence selected from the group consisting of SEQ ID NOs: 14, 18, 20, 22, and 24. Preferably, the plant or seed is one or more of maize, soybean, canola, oil seed rape, cotton, sesame, flax, peanut, sunflower, safflower, olive, and oil palm.

Preferably, the plant or seed of the present invention is processed. More preferably, the plant or seed is used to produce a product, such as, for example, feed, meal, oil, or protein. The plant or seed used in this context is comprised of a DNA construct that includes a heterologous promoter that functions in a plant cell and a nucleic acid molecule selected from the group consisting of SEQ ID NOs: 11, 12, 13, 16, 17, 19, 21, and 23.

In another embodiment, the plant or seed of the present invention is comprised of the DNA construct comprising an expression cassette comprising a heterologous promoter that functions in a plant cell operably linked to a nucleic acid molecule that encodes a polypeptide molecule, which polypeptide molecule comprises a polypeptide sequence selected from the group consisting of SEQ ID NOs: 14, 18, 20, 22, and 24. Preferably, the plant or seed of the invention is processed into a product, which product may be feed, meal, oil, and protein.

The present invention further provides methods for the production of DGAT2 proteins in a host cell or progeny thereof. Recombinant cells containing DGAT2 are also provided.

The present invention provides a method of producing a plant having enhanced oil composition comprising the steps of transforming a plant cell with a DNA construct expressing diacylglycerol acyltransferase and regenerating said plant cell into a fertile plant relative to a plant having a similar genetic background but lacking the introduced nucleic acid molecule. The present invention also includes a fertile plant providing seeds having an increased oil yield relative to a plant having a similar genetic background but lacking the introduced nucleic acid molecule.

In another aspect, the present invention provides a polynucleotide encoding a polypeptide having at least one of the amino acid motifs: AYVFGYEPHSVXPI (SEQ ID NO: 33) and FXXPXYR (SEQ ID NO: 34), where X represents any amino acid. Such polypeptides include, for example, SEQ ID NOs: 14, 18, 20, 22, and 24.

In still yet another aspect, the present invention provides a polypeptide, including fragments and proteins, having diacylglycerol acyltransferase activity and which polypeptide comprises at least one of the amino acid motifs: AYVFGYEPHSVXPI (SEQ ID NO: 33) and FXXPXYR (SEQ ID NO: 34), where X represents any amino acid. Such polypeptides include, for example, SEQ ID NOs: 14, 18, 20, 22, and 24.

BRIEF DESCRIPTION OF THE SEQUENCE LISTING

SEQ ID NO: 1 DNA sequence of *Mortierella ramanniana* DGAT2A
SEQ ID NO: 2 polypeptide sequence of *Mortierella ramanniana* DGAT2A
SEQ ID NO: 3 DNA sequence of *Mortierella ramanniana* DGAT2B
SEQ ID NO: 4 polypeptide sequence of *Mortierella ramanniana* DGAT2B
SEQ ID NO: 5 DNA sequence of *Saccharomyces cerevisiae* DGAT2B
SEQ ID NO: 6 polypeptide sequence of *Saccharomyces cerevisiae* DGAT2B
SEQ ID NO: 7 DNA primer for NcDGAT2
SEQ ID NO: 8 DNA primer for NcDGAT2
SEQ ID NO: 9 DNA primer for NcDGAT2
SEQ ID NO: 10 DNA primer for NcDGAT2
SEQ ID NO: 11 DNA sequence for *Mortierella ramaniana* DAGT2B.nno
SEQ ID NO: 12 DNA sequence for *Neurospora crassa* DGAT.nno
SEQ ID NO: 13 DNA sequence for *Neurospora crassa* DGAT2
SEQ ID NO: 14 polypeptide sequence for *Neurospora crassa* DGAT2
SEQ ID NO: 15 DNA sequence of *Mortierella ramanniana* DGAT2A.nno
SEQ ID NO: 16 DNA sequence of *Saccharomyces cerevisiae* DGAT2.nno
SEQ ID NO: 17 DNA sequence of *Hordeum vulgare* DGAT2
SEQ ID NO: 18 polypeptide sequence of *Hordeum vulgare* DGAT2
SEQ ID NO: 19 DNA sequence of *Zea mays* DGAT2
SEQ ID NO: 20 polypeptide sequence of *Zea mays* DGAT2
SEQ ID NO: 21 DNA sequence of *Glycine max* DGAT2
SEQ ID NO: 22 polypeptide sequence of *Glycine max* DGAT2
SEQ ID NO: 23 DNA sequence of *Triticum aestivum* DGAT2
SEQ ID NO: 24 polypeptide sequence of *Triticum aestivum* DGAT2
SEQ ID NO: 25 DNA sequence of *Drosophila melanogaster* DGAT
SEQ ID NO: 26 polypeptide sequence of *Drosophila melanogaster* DGAT SEQ ID NO: 27 DNA sequence of *Homo sapiens* DGAT SEQ ID NO: 28 polypeptide sequence of *Homo sapiens* DGAT SEQ ID NO: 29 polypeptide sequence of *Schizosaccharomyces pombe*1 DGAT2

SEQ ID NO: 30 polypeptide sequence of *Schizosaccharomyces pombe*2 DGAT2

SEQ ID NO: 31 polypeptide sequence of *Candida albicans* DGAT2

SEQ ID NO: 32 polypeptide sequence of *Arabidopsis thaliana* DGAT2

BRIEF DESCRIPTION OF THE DRAWINGS

FIGS. 1*a*, 1*b*, and 1*c* collectively show the sequence alignment of certain derived DGAT2 polypeptide sequences. Similar sequences between polypeptides can be used to identify like molecules with similar activities. Several computer programs can be used to identify conserved, sequence motifs between related molecules, including but not limited to MEME, or GENE SCAN. Once the sequence motifs are identified, their function can be assayed. For example, motif sequences in DGAT can be used to identify other DGAT polypeptides. Novel motifs can be derived from the polypeptide sequences disclosed in the present invention and used to screen sequence databases or in the design of degenerate nucleic acid probes to isolate novel DNA molecules that encode for DGAT. The amino acid sequences of the predicted DGAT2 polypeptides are aligned using the Clustal multiple sequence alignment program. Totally conserved residues are shaded black, grey shaded is the consensus of three or more sequences. All sequences are full-length. Residues shown above the alignment are highly conserved signature amino acids found in the motifs D and E of the acyltransferase (Neuwald, *Curr. Biol.*, 7:465-466, (1997)). In this area, DGAT2 and the acyltransferase superfamily sequences co-align, only the shared conserved amino acid residues are shown. Key: MrDGAT2A (SEQ ID NO: 2), MrDGAT2B (SEQ ID NO: 4), ScDGAT2B (SEQ ID NO: 6); NcDGAT2 (SEQ ID NO: 14), ZmDGAT2 (SEQ ID NO: 20), GmDGAT2 (SEQ ID NO: 22), HvDGAT2 (SEQ ID NO: 18), TaDGAT2 (SEQ ID NO: 24), CaDGAT2 (SEQ ID NO: 31), and AtDGAT2 (SEQ ID NO: 32).

Figure 12A:
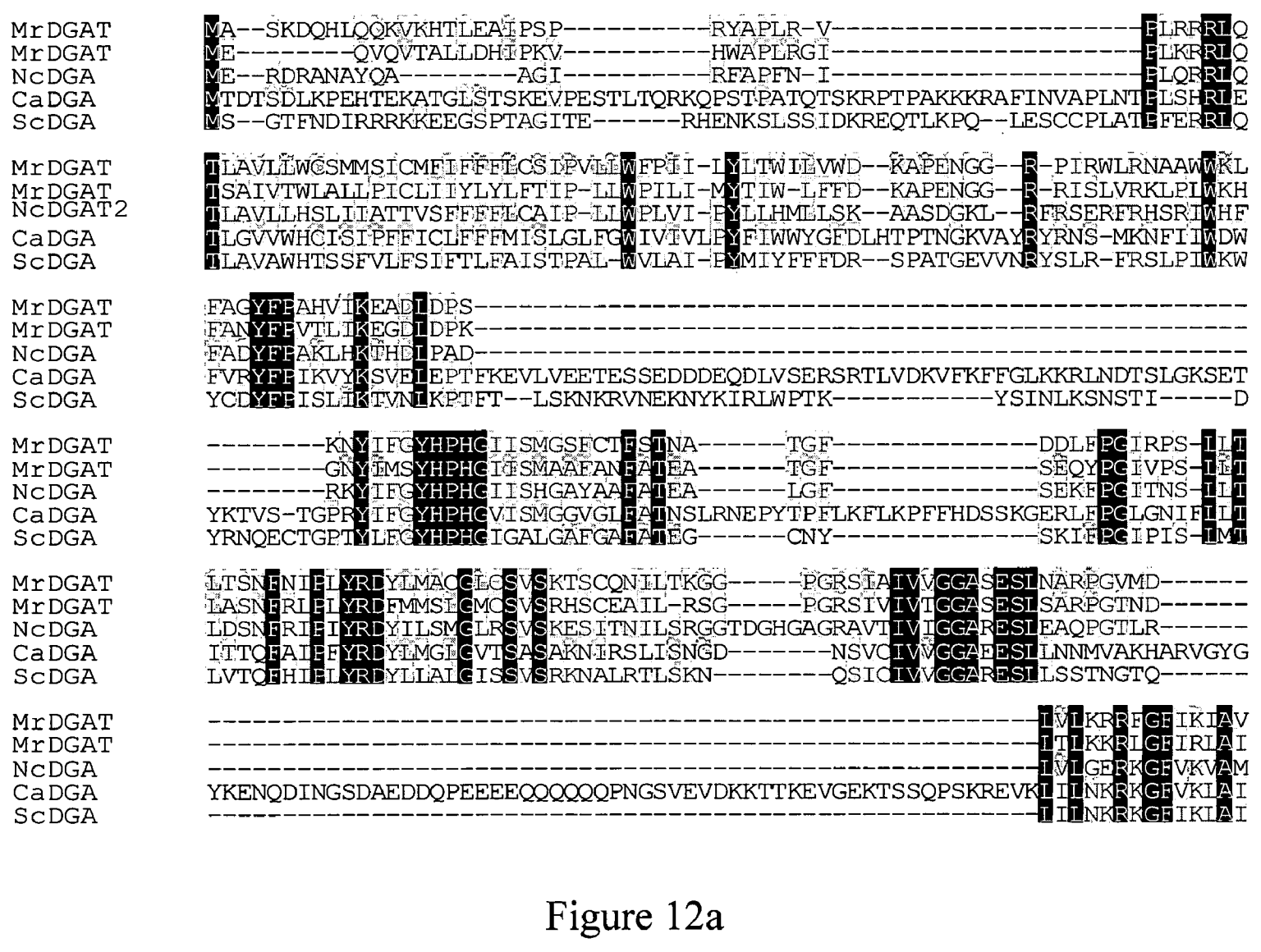

FIGS. 12*a* and 12*b* show the sequence alignment of derived DGAT2 polypeptide sequences from certain fungal species, as identified therein. The information for how to read this figure, including the meaning of abbreviations and shadings used, is the same as stated above for FIGS. 1*a*, 1*b*, and 1*c*. The conserved regions indicated in shadings and black are usefully employed to identify other DGAT2 polypeptides derived from other species. In particular, analysis of these sequences reveals the following motif: FXXPXYR (SEQ ID NO: 34), where X represents any amino acid, which can be used to identify further DGAT2 sequences, preferably those of fungal origin.

Figure 13:
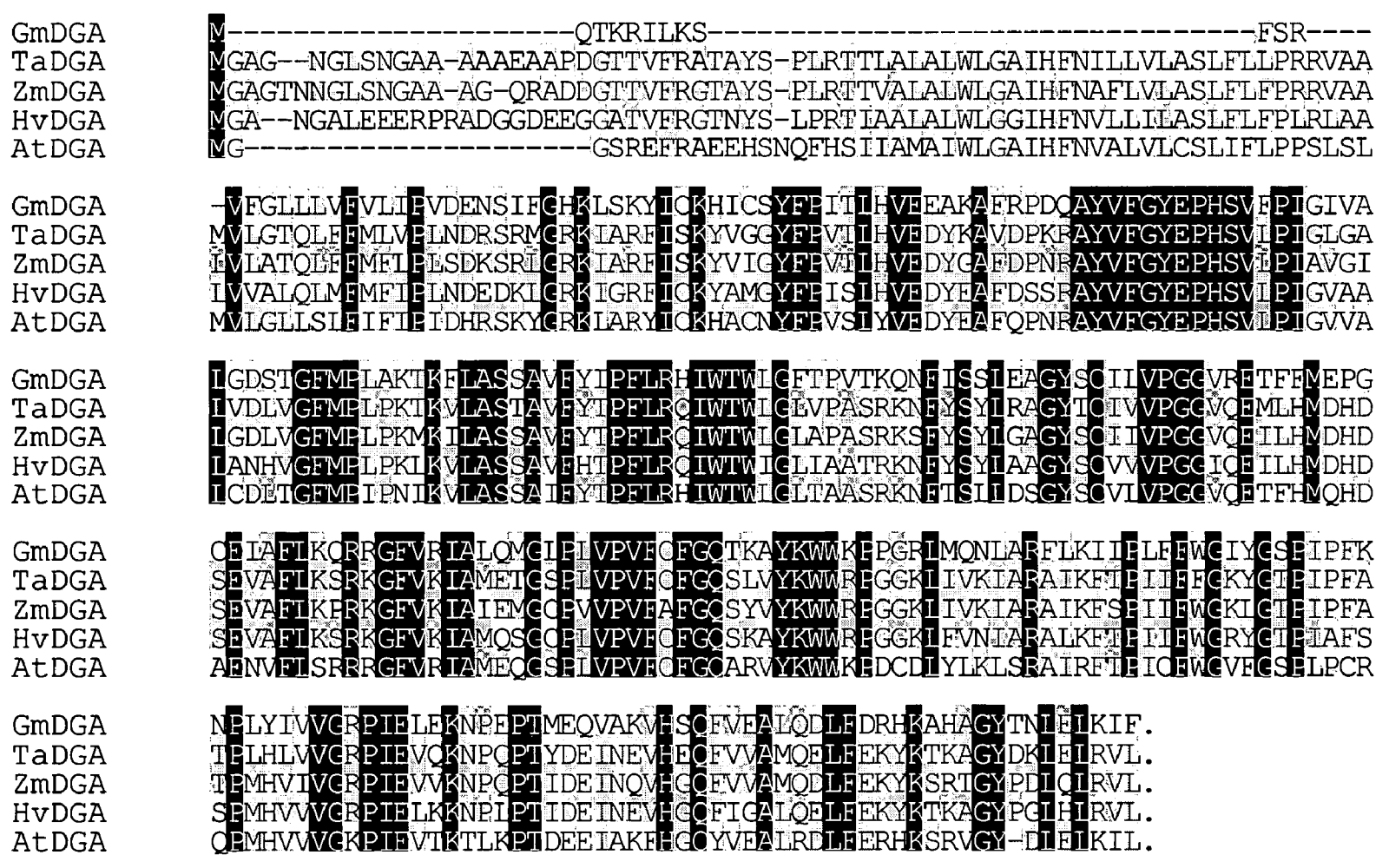

FIG. 13 shows the sequence alignment of derived DGAT2 polypeptide sequences from certain plant species, as identified therein. The information for how to read this figure, including the meaning of abbreviations and shadings used, is the same as stated above for FIGS. 1*a*, 1*b*, and 1*c*. The conserved regions indicated in shadings and black are usefully employed to identify other DGAT2 polypeptides derived from other species. In particular, analysis of these sequences reveals the following motif: AYVFGYEPHSVXPI (SEQ ID NO: 33), which can be used to identify further DGAT2 sequences, preferably those of plant origin.

DETAILED DESCRIPTION OF THE INVENTION

Figures 2, 3:
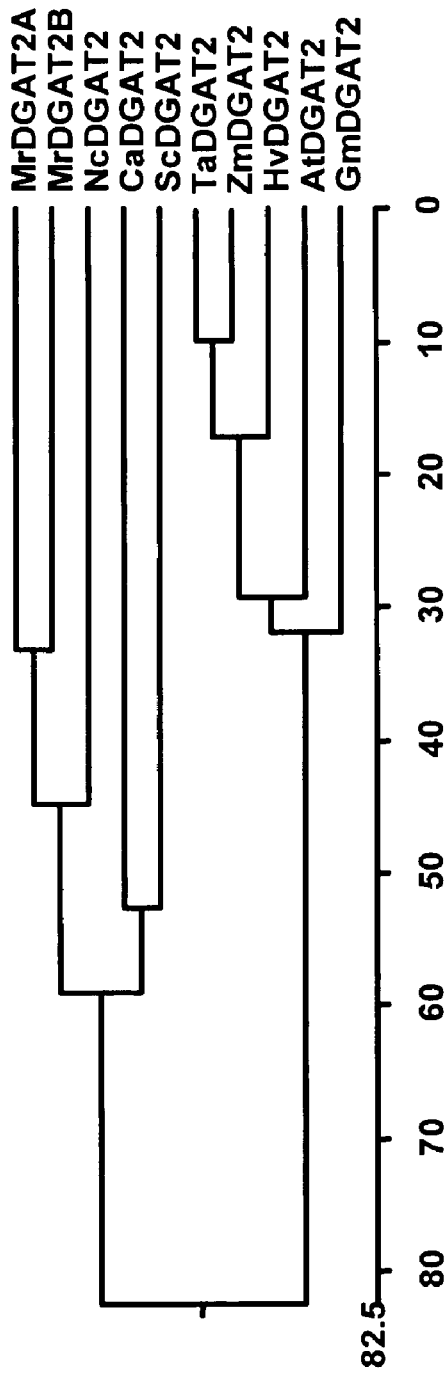
FIG. 2 shows the phylogenetic tree of DGAT2 family members of FIG. 1. The tree is constructed using the DNASTAR software.
FIG. 3 is a listing of DNA primer molecules used in the invention.
Figure 4:
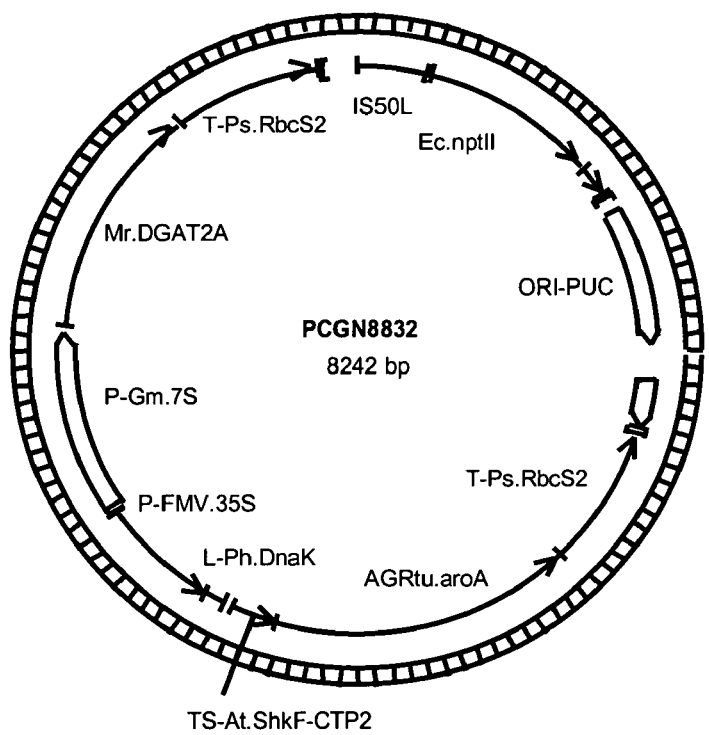
FIG. 4 is a schematic of vector pCGN8832.
Figure 5:
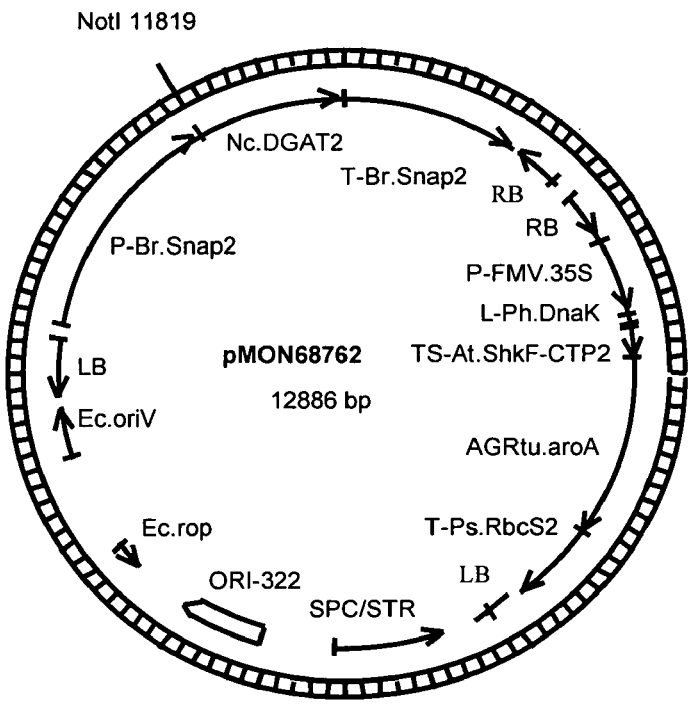
FIG. 5 is a schematic of vector pMON68762.

As used herein, the term triacylglycerol composition means a compound in an organism that includes the water-insoluble, fatty acid triesters of glycerol, i.e., having the chemical formula $(CH_2-R)_3$ where R is an ester.

As used herein, the term DGAT1 refers to a DGAT protein as described in U.S. Pat. No. 6,444,876, herein incorporated by reference in its entirety, which is related to the acyl CoA: cholesterol acyltransferase (ACAT) gene family and is responsible for transferring an acyl group from acyl-coenzyme-A to the sn-3 position of 1,2-diacylglycerol (DAG) to form triacylglycerol (TAG).

As used herein, the term DGAT2 refers to a non-DGAT1 protein as defined above where the protein responsible for transferring an acyl group from acyl-coenzyme-A to the sn-3 position of 1,2-diacylglycerol (DAG) to form triacylglycerol (TAG). DGAT2 proteins typically are generally less than 40 kD in weight, and typically in the 33-42 kD range.

As used herein, the term DGAT2A refers to a *Mortierella ramanniana* DGAT2 that has an amino acid sequence of SEQ ID NO: 2. As used herein, the term DGAT2B refers to a *Mortierella ramanniana* DGAT2 that has an amino acid sequence of SEQ ID NO: 4.

As used herein, the phrase "oil composition" means the ratio of different fatty acid or oil components within a sample. Such a sample may be a plant or plant part, such as a seed. Such a sample may also be a collection of plant parts.

As used herein, the phrase "percentage content" in a preferred embodiment means the percent by total weight of a particular component, relative to other similar or related components.

As used herein, the phrase "enhanced oil" includes increased oil yield or altered oil composition.

As used herein, a diacylglycerol acyltransferase (DGAT) gene of the present invention includes any nucleic acid sequence encoding amino acids, such as protein, polypeptide, or peptide, obtainable from a cell source, which demonstrates the ability to catalyze the production of triacylglycerol from 1,2-diacylglycerol and fatty acyl substrates under enzyme reactive conditions. By "enzyme reactive conditions" it is meant that any necessary conditions are available in an environment (i.e., such factors as temperature, pH, lack of inhibiting substances) that will permit the enzyme to function.

The present invention relates to acyl CoA:diacylglycerol acyltransferase (referred to herein as DGAT) which catalyzes the final step in the production of triacylglycerol (TAG). More particularly, the present invention includes DGAT polypeptides and polynucleotides that encode the DGAT polypeptides. The DGAT polypeptide and polynucleotide molecules of the present invention are isolated from plant and fungal sources. Expression of the cDNAs in insect and plant cells conferred high levels of DGAT activity on the membranes isolated from these cells. The present invention provides a gene family, including members in fungi, plants, and animals, which encode enzymes with DGAT function.

DGAT proteins are isolated from cells of the oleaginous fungus *Mortierella ramanniana*. Following cell lysis, DGAT activity is associated with the lipid body fraction and detergent solubilization is required to release the membrane-bound proteins to permit their purification using traditional chromatographic techniques. A stimulation of DGAT activity in the homogenate is observed following the addition of the detergent Triton X-100. Using a 5-step protocol, two proteins, 36 kD and 36.5 kD by SDS-PAGE, are identified as being associated with DGAT activity. These proteins are named MrDGAT2A and MrDGAT2B, respectively. Final specific activity recoveries of 1.6% and 4.2%, respectively, are reported for the purest, most active fractions containing each protein. Expression of the cloned cDNAs in insect cells confirmed DGAT. Full-length clones are obtained for several plant and fungal DGAT homologs and the expressed proteins are evaluated in insect cells or plant cells. The homologs tested exhibited some level of DGAT activity demonstrating that the genes in this family are related by function.

The present invention provides a number of agents, for example, nucleic acid molecules and polypeptides associated with enzymes responsible for transferring an acyl group from acyl-coenzyme-A to the sn-3 position of 1,2-diacylglycerol (DAG) to form triacylglycerol (TAG), and provides uses of such agents.

Nucleic Acid Molecules

Agents of the invention include nucleic acid molecules. In a preferred aspect of the present invention the nucleic acid molecule comprises a nucleic acid sequence selected from the group consisting of SEQ ID NOs: 11, 12, 13, 16, 17, 19, 21,.23, 25, and 27.

In a further aspect of the present invention the nucleic acid molecule comprises a nucleic acid sequence encoding an amino acid sequence selected from the group consisting of SEQ ID NOs: 14, 18, 20, 22, 24, 26, 28, and fragments thereof.

A preferred embodiment of the present invention relates to the use of motifs, i.e., conserved elements found in the sequences of identified DGAT molecules, for the purpose of identifying other DGAT genes and proteins. Accordingly, one skilled in the art can use a motif, such as, for example SEQ ID NO: 33 or 34, with or without reverse transcribing the motif sequence, and screen for other genes that encode a DGAT or other polypeptides that have DGAT activity.

A first nucleic acid sequence of the present invention displays "substantial identity" to a reference nucleic acid sequence if, when optimally aligned (with appropriate nucleotide insertions or deletions totaling less than 20% of the reference sequence over the window of comparison) with the other nucleic acid (or its complementary strand), there is at least about 75% nucleotide sequence identity, preferably at least about 80% identity, more preferably at least about 85% identity, yet more preferably at least about 90%, and most preferably at least about 95% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman, *Adv. Appl. Math.*, 2:482 (1981); by the homology alignment algorithm of Needleman and Wunsch, *J. Mol. Biol.*, 48:443 (1970); by the search for similarity method of Pearson and Lipman, *Proc. Natl. Acad. Sci.* (*U.S.A.*), 85:2444 (1988); preferably by computerized implementations of these algorithms (GAP, BESTFIT, FASTA, and TFASTA) in the Wisconsin Genetics Software Package Release 7.0, Genetics Computer Group, 575 Science Dr., Madison, Wis. The reference nucleic acid may be a full-length molecule or a portion of a longer molecule. Alternatively, two nucleic acids have substantial identity if one hybridizes to the other under stringent conditions.

It is understood that in a further aspect of the present invention, the nucleic acid sequences can encode a protein that differs from any of the proteins in that one or more amino acids have been deleted, substituted, or added without altering the function. For example, it is understood that codons capable of coding for such conservative amino acid substitutions are known in the art.

One subset of the nucleic acid molecules of the present invention is fragment nucleic acid molecules. Fragment nucleic acid molecules may consist of significant portion(s) of, or indeed most of, the nucleic acid molecules of the present invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the present invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using a program such as GeneUp (Pesole et al., *BioTechniques*, 25:112-123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 11, 12, 13, 16, 17, 19, 21, 23, 25, and 27, and complements thereof. Nucleic acid molecules of the present invention also include those that specifically hybridize to nucleic acid molecules encoding an amino acid sequence selected from SEQ ID NOs: 14, 18, 20, 22, 24, 26, 28, and fragments thereof.

A nucleic acid molecule is said to be the "complement" of another nucleic acid molecule if the molecules exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 20-25° C., are known to those skilled in the art or can be found in *Current Protocols in Molecular Biology*, John Wiley & Sons, New York (1989), 6.3.1-6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 11, 12, 13, 16, 17, 19, 21, 23, 25, and 27, and complements thereof under moderately stringent conditions, for example at about 2.0× SSC and about 65° C.

A nucleic acid molecule of the present invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is selected from the group consisting of alfalfa, *Arabidopsis*, barley, *Brassica campestris*, oilseed rape, broccoli, cabbage, canola, citrus, cotton, garlic, oat, Allium, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, *Phaseolus*, crambe, mustard, castor bean, sesame, cottonseed, linseed, safflower, and oil palm. More particularly, preferred homologs are selected from canola, corn, *Brassica campestris*, oilseed rape, soybean, crambe, mustard, castor bean, peanut, sesame, cottonseed, linseed, rapeseed, safflower, oil palm, flax, and sunflower. In an even more preferred embodiment, the homolog is selected from the group consisting of canola, rapeseed, corn, *Brassica campestris*, oilseed rape, soybean, sunflower, safflower, oil palms, and peanut. In a particularly preferred embodiment, the homolog is soybean. In a particularly preferred embodiment, the homolog is canola. In a particularly preferred embodiment, the homolog is oilseed rape.

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any disclosed nucleic acid or amino acid sequence may be modified to reflect the codon usage of a host cell or organism in which they are contained. Modification of a structural nucleic acid sequence for codon usage in plants is described, for example in U.S. Pat. Nos. 5,689,052 and 5,500,365.

In a preferred embodiment, any of the nucleic acid molecules of the present invention can be operably linked to a promoter region that functions in a plant cell to cause the production of an mRNA molecule, where the nucleic acid molecule that is linked to the promoter is heterologous with respect to that promoter. As used herein, "heterologous" means not naturally occurring together.

Protein and Peptide Molecules

A class of agents includes one or more of the polypeptide molecules encoded by a nucleic acid agent of the present invention. Another class of agents includes one or more polypeptide molecules of the present invention. A particular preferred class of proteins is that having an amino acid sequence selected from the group consisting of SEQ ID NOs: 14, 18, 20, 22, 24, 26, and 28, and fragments thereof. Polypeptide agents may have C-terminal or N-terminal amino acid sequence extensions.

As used herein, the terms "protein," "peptide molecule," or "polypeptide" includes any molecule that comprises five or more amino acids. It is well known in the art that protein, peptide, or polypeptide molecules may undergo modification, including post-translational modifications, such as, but not limited to, disulfide bond formation, glycosylation, phosphorylation, or oligomerization. Thus, as used herein, the terms "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

In a further aspect of the present invention, the DGAT2 proteins of the present invention have been solubilized. "Solubilization" refers to the extraction of the DGAT enzyme from the membranes in such a way that it then behaves in a manner typical of enzymes that are not membrane-associated.

It should also be noted that plant DGAT proteins from a variety of sources can be used to investigate TAG biosynthesis in a wide variety of in vivo applications. Because all plant seeds appear to synthesize lipids via a common metabolic pathway, the study and/or application of one plant DGAT protein to a heterologous plant host may be readily achieved in a variety of species. In other applications, a plant DGAT protein can be used outside the native plant source of the DGAT protein to enhance the production and/or modify the composition of the TAG produced or synthesized in vitro.

The percentage of sequence identity is determined by comparing two optimally aligned sequences over a comparison window, wherein the portion of the polynucleotide or amino acid sequence in the comparison window may comprise additions or deletions (i.e., gaps) as compared to the reference sequence (that does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by one hundred to yield the percentage of sequence identity.

A polypeptide or polynucleotide molecule can be substantially identical or substantially homologous to related molecules. These homologues with substantial identity to a related molecule generally comprise at least one polypeptide sequence or one polynucleotide sequence that has at least 70% sequence identity compared to other polypeptide sequences or polynucleotide sequences. The Gap program in the WISCONSIN PACKAGE version 10.0-UNIX from Genetics Computer Group, Inc. based on the method of Needleman and Wunsch (*J. Mol. Biol.*, 48:443-453 (1970)) using the set of default parameters for pairwise comparison (for amino acid sequence comparison: Gap Creation Penalty=8, Gap Extension Penalty=2; for nucleotide sequence comparison: Gap Creation Penalty=50; Gap Extension Penalty=3); or using the TBLASTN program in the BLAST 2.2.1 software suite (Altschul et al., *Nucleic Acids Res.*, 25:3389-3402), using BLOSUM62 matrix (Henikoff and Henikoff, *Proc. Natl. Acad. Sci.* (*U.S.A.*), 89:10915-10919 (1992)) and the set of default parameters for pair-wise comparison (gap creation cost=11, gap extension cost=1). In BLAST, the E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by "BLASTing" against public databases, such as GenBank, have generally increased over time for any given query/entry match. Percent identity with respect to proteins refers to the percentage of identically matched amino acid residues that exist along the length of that portion of the sequences which is aligned by the BLAST algorithm.

One aspect of the present invention provides an isolated polynucleic acid molecule comprising a nucleotide sequence or complement thereof, wherein the nucleotide sequence encodes a polypeptide that is substantially homologous to a protein amino acid sequence of the present invention, wherein substantially homologous is defined as at least about 50%, or at least about 60%, or at least about 70%, or at least about 75%, or at least about 80% sequence identity, or at least about 85% or at least about 90% sequence identity, or at least about 95% sequence identity, or at least about 98% sequence identity to a member selected from the group consisting of SEQ ID NOS: 14, 18, 20, 22, and 24.

Agents of the invention include proteins and fragments thereof comprising at least about a contiguous 10 amino acid region preferably comprising at least about a contiguous 20 amino acid region, even more preferably comprising at least a contiguous 25, 35, 50, 75, or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

In addition to isolation of other DGAT proteins or genes, genes for other related acyltransferase proteins can also be obtained using the sequence information from the DGAT sequences of the present invention and related nucleic acid or amino acid sequences. For example, *Schizosaccharomyces pombe* amino acid sequence homologs of DGAT2 proteins comprising the amino acids SEQ ID NOs: 29 and 30 are disclosed. In another example, other acyltransferase enzymes are involved in plant lipid biosynthesis, including lysophosphatidylcholine acyltransferase (LPCAT), lysophosphatidylserine acyltransferase (LPSAT), lysophosphatidylethanolamine acyltransferase (LPEAT), phosphatidylcholine diacylglycerol acyltransferase (PDAT), and lysophosphatidylinositol acyltransferase (LPIAT).

DNA Constructs and Plant Transformants

One or more of the nucleic acid molecules of the present invention may be used in plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism. Bacterial plasmid maintainance elements are components of DNA constructs. These elements comprise antibiotic markers, i.e., the aadA gene (SPC/STR, spectomycin, and streptomycin resistance), Ec.nptII (neomycin phosphotransferase, kanamycin resistance); origins of replication or elements that control plasmid copy number, i.e., Ec.oriV, Ec.ori322, ORI-PUC, and Ec.ROP. Additional information on these elements can be obtained from Sambrook et al., *Molecular Cloning, A Laboratory Manual*, 2nd Ed., Cold Spring Harbor Press, Cold Spring Harbor, N.Y. (1989), among others.

In a preferred aspect of the present invention the exogenous genetic material comprises a nucleic acid sequence selected from the group consisting of SEQ ID NOs: 11, 12, 13, 16, 17, 19, 21, 23, and complements thereof, and fragments of either. In a further aspect of the present invention the exogenous genetic material comprises a nucleic acid sequence encoding an amino acid sequence selected from the group consisting of SEQ ID NOs: 14, 18, 20, 22, 24, and fragments thereof.

In an embodiment of the present invention, exogenous genetic material comprised of one or more genes is introduced into a plant. In one embodiment, preferred combinations of genes include, but are not limited to, one or more of the following genes: MrDGAT2A (SEQ ID NO: 1), MrDAGAT2A.nno (SEQ ID NO: 15), MrDGAT2B (SEQ ID NO: 3), MrDGAT2B.nno (SEQ ID NO: 11), ScDGAT2 (SEQ ID NO: 5), ScDGAT2.nno (SEQ ID NO: 16), NcDGAT2 (SEQ ID NO: 13), and NcDGAT.nno (SEQ ID NO: 12). In another embodiment, preferred combinations of genes include, but are not limited to, one of the following genes expressed under the control of two separate promoters: MrDGAT2A (SEQ ID NO: 1), MrDAGAT2A.nno (SEQ ID NO: 15), MrDGAT2B (SEQ ID NO: 3), MrDGAT2B.nno (SEQ ID NO: 11), ScDGAT2 (SEQ ID NO: 5), ScDGAT2.nno (SEQ ID NO: 16), NcDGAT2 (SEQ ID NO: 13), and NcDGAT.nno (SEQ ID NO: 12).

In such combinations, one or more of the gene products can be localized in the cytoplasm. Such genes can be introduced, for example, on a single construct in either a monocistronic or polycistronic arrangement, introduced on different constructs but in the same transformation event, or introduced into separate plants followed by one or more crosses to generate the desired combination of genes.

Such genetic material may be transferred into either monocotyledons or dicotyledons including, but not limited to canola, corn, soybean, *Arabidopsis, Phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee, and dioscorea (Christou, In: *Particle Bombardment for Genetic Engineering of Plants*, Biotechnology Intelligence Unit, Academic Press, San Diego, Calif. (1996), with canola, corn, *Brassica campestris*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris*, oilseed rape, soybean, sunflower, safflower, oil palms, and peanut preferred. In a preferred embodiment, the homolog is selected from the group consisting of maize, soybean, canola, cottonseed, sesame, flax, peanut, sunflower, safflower, and oil palm. In a more preferred embodiment, the genetic material is transferred into canola. In another more preferred embodiment, the genetic material is transferred into oilseed rape. In another particularly preferred embodiment, the genetic material is transferred into soybean.

Transfer of a nucleic acid molecule that encodes a protein can result in expression or overexpression of that polypeptide in a transformed cell or transgenic plant. One or more of the proteins or fragments thereof encoded by nucleic acid molecules of the present invention may be overexpressed in a transformed cell or transformed plant. Such expression or overexpression may be the result of transient or stable transfer of the exogenous genetic material.

In a preferred embodiment, expression or overexpression of a polypeptide of the present invention in a plant provides in that plant, relative to an untransformed plant with a similar genetic background, an association with an increase in DGAT activity.

The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds, and flowers. A preferred organ is a seed.

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

A construct or vector may include a plant promoter to express the polypeptide of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.*, 1:209:219 (1991)), phaseolin (Bustos et al., *Plant Cell*, 1(9): 839-853 (1989)), soybean trypsin inhibitor (Riggs et al., *Plant Cell*, 1(6):609-621 (1989)), ACP (Baerson et al., *Plant Mol. Biol.*, 22(2):255-267 (1993)), stearoyl-ACP desaturase (Slocombe et al., *Plant Physiol.*, 104(4): 167-176 (1994)), soybean a' subunit of β-conglycinin (P-Gm7S, see, for example, Chen et al., *Proc. Natl. Acad. Sci.*, 83:8560-8564 (1986)), *Vicia faba* USP (P-Vf.Usp, see, for example, SEQ ID NOS: 1,2, and 3, U.S. Pat. No. 7,078,588), and *Zea mays* L3 oleosin promoter (P-Zm.L3, see, for example, Hong et al., *Plant Mol. Biol.*, 34(3):549-555 (1997)), Also included are the zeins, which are a group of storage proteins found in corn endosperm. Genomic clones for zein genes have been isolated (Pedersen et al., *Cell*, 29:1015-1026 (1982), and Russell et al., *Transgenic Res.*, 6(2):157-168) and the promoters from these clones, including the 15 kD, 16 kD, 19 kD, 22 kD, 27 kD, and genes, could also be used. Other promoters known to function, for example, in corn include the promoters for the following genes: wary, *Brittle, Shrunken* 2, Branching enzymes I and II, starch synthases, debranching enzymes, oleosins, glutelins, and sucrose synthases. A particularly referred promoter for corn endosperm expression is the promoter for the glutelin gene from rice, more particularly the Osgt-1 promoter (Zheng et al., *Mol. Cell Biol.*, 13:5829-5842 (1993)). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins, and the aleurone specific proteins. A preferred promoter for expression in the seed is a napin promoter, referred to herein as P-Br.Snap2. Another preferred promoter for expression is an Arcelin5 promoter (U.S. Pat. No. 6,927,321). Yet another preferred promoter is a soybean 7S promoter (P-Gm.7S) and the soybean 7Sα' beta conglycinin promoter (P-Gm.Sphas1).

Promoters, which can cause the overexpression of the polypeptide of the present invention, are generally known in the art, e.g., viral promoters (P-CaMV35S, U.S. Pat. No. 5,352,605; P-FMV35S, and its enhancer element E-FMV35S identified as the 5' portion of the P-FMV35S without the native start of transcription, U.S. Pat. Nos. 5,378,619 and 5,018,100, and chimeric promoter molecules described in U.S. Pat. No. 6,462,258 as SEQ ID NO: 28 referrerd to in the present invention as E-FMV35S/P-At.Tsf1), and various plant derived promoters, e.g., plant actin promoters (P-Os-.Act1, and genetic elements derived therefrom, U.S. Pat. Nos. 5,641,876 and 6,429,357).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell*, 1:977-984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell*, 1:671-680 (1989); Bevan et al., *Nucleic Acids Res.*, 11:369-385 (1983)). Regulatory transcript termination regions can be provided in plant expression constructs of this present invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include additional regulatory elements. Examples of such include the translation leader isolated from *Petunia hybrida* Hsp70 gene (L-Ph.D-naK, U.S. Pat. No. 5,362,865), the Adh intron 1 (Callis et al., *Genes and Develop.*, 1: 1183-1200 (1987)), the sucrose synthase intron (Vasil et al., *Plant Physiol.*, 91:1575-1579 (1989)), the rice actin intron (I-Os.Act1 U.S. Pat. No. 5,641,876), and the TMV omega element (Gallie et al., *The Plant Cell*, 1:301-311 (1989)). Transcriptional termination regions, e.g., the 3' untranslated region from the *Brassica rapa*, T-Br-.Snap2. These and other regulatory elements may be included when appropriate.

A vector or construct may also include a selectable marker. Selectable markers may also be used to select for plants or plant cells that contain the exogenous genetic material. Examples of such include, but are not limited to: a nptII gene (Potrykus et al., *Mol. Gen. Genet.*, 199:183-188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology*, 6:915-922 (1988); Reynaerts et al., Selectable and Screenable Markers. In Gelvin and Schilperoort; Plant Molecular Biology Manual, Kluwer, Dordrecht (1988); Reynaerts et al., Selectable and Screenable Markers. In Gelvin and Schilperoort; Plant Molecular Biology Manual, Kluwer, Dordrecht (1988); a nitrilase gene which confers resistance to bromoxynil (Stalker et al., *J. Biol. Chem.*, 263:6310-6314 (1988)); a mutant acetolactate synthase gene (ALS) which confers imidazolinone or sulphonylurea resistance (European Patent Application 154,204 (Sep. 11, 1985)), ALS (D'Halluin et al., *Bio/Technology*, 10:309-314 (1992)), and a methotrexate resistant DHFR gene (Thillet et al., *J. Biol. Chem.*, 263:12500-12508 (1988)). A particularly preferred marker is glyphosate tolerance, this can be achieved in plants by expressing a glyphosate resistant EPSPS, for example, the aroA-CP4 coding sequence from *Agrobacterium tumefaciens* (U.S. Pat. No. 5,633,435), herein referred to as AGRtu.aroA. The AGRtu.aroA coding sequence is linked to a chloroplast transit peptide (CTP), for example the CTP2 coding sequence isolated from the *Arabidopsis* ShkF gene, herein referred to as TS-At.ShkF-CTP2.

In a preferred embodiment of the present invention, a transgenic plant expressing the desired protein is to be produced. Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species. The transgene(s) are constructed in a DNA plasmid vector and are usually bordered by an *Agrobacterium* Ti plasmid right border DNA region (RB) and a left border DNA region (LB). During the process of *Agrobacterium* mediated transformation the DNA plasmid is nicked by VirD1 and VirD2 endonucleases at the right and left border regions and the T-DNA region is inserted into the plant genome.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880; and 5,610,042; each of which is specifically incorporated herein by reference in its entirety), particles are coated with nucleic acids and delivered into cells by a propelling force. Exemplary particles include those comprised of tungsten, platinum, and preferably, gold.

Microprojectile bombardment techniques are widely applicable, and may be used to transform virtually any plant species. Examples of species that have been transformed by microprojectile bombardment include monocot species such as maize, barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin; and tetracycline.

The regeneration, development, and cultivation of plants from various transformed explants is well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, *Physiol. Plant*, 15:473-497 (1962)) or N6-based media (Chu et al., *Scientia Sinica*, 18:659 (1975)) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared, and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Anti-sense suppression of genes in plants by introducing by transformation of a construct comprising DNA of the gene of interest in an anti-sense orientation is disclosed in U.S. Pat. Nos. 5,107,065; 5,453,566; 5,759,829; 5,874,269; 5,922,602; 5,973,226; and 6,005,167; all of which are incorporated herein by reference.

Co-suppression of genes in a plant by introducing by transformation of a construct for cytoplasmic expression comprising DNA of the gene of interest in a sense orientation is disclosed, for example, in U.S. Pat. Nos. 5,034,323; 5,231,020; 5,283,184; and 6,271,033, all of which are incorporated herein by reference.

Antisense approaches are a way of preventing or reducing gene function by targeting the genetic material (Mol et al., *FEBS Lett.*, 268:427-430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), New York: *Plenum* 11:49-63 (1989)).

The present invention also provides for parts of the plants, particularly reproductive or storage parts, of the present invention. Plant parts, without limitation, include seed, endosperm, ovule, and pollen. In a particularly preferred embodiment of the present invention, the plant part is a seed. In one embodiment the seed is a constituent of animal feed.

Any of the plants or parts thereof of the present invention that can provide a processed product comprising feed, meal, protein, flour, fiber, extactable nutrients, or oil preparation. A particularly preferred plant part for this purpose is a seed. In a preferred embodiment the processed product is designed for livestock animals or humans, or both. Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227, herein incorporated by reference. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10, or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75%, or 90% by volume or weight of the oil component of any product. In another embodiment, the oil preparation may be blended and can constitute greater than 10%, 25%, 35%, 50%, or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A breeding program can be enhanced using marker-assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

Exemplary Uses

Nucleic acid molecules and fragments thereof of the present invention may be employed to obtain other nucleic acid molecules from the same species (nucleic acid molecules from corn may be utilized to obtain other nucleic acid molecules from corn). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the present invention may also be employed to obtain nucleic acid homologs. Such homologs include the nucleic acid molecules of plants and other organisms, including bacteria and fungi, including the nucleic acid molecules that encode, in whole or in part, protein homologs of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of the sequences selected from the group consisting of SEQ ID NOs: 11, 12, 13, 16, 17, 19, 21, 23, 25, and 27, and complements thereof, because complete complementarity is not needed for stable hybridization. The nucleic acid molecules of the present invention therefore also include molecules that, although capable of specifically hybridizing with the nucleic acid molecules, may lack "complete complementarity."

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci. (U.S.A.)*, 85:8998-9002 (1988); Ohara et al., *Proc. Natl. Acad. Sci. (U.S.A.)*, 86:5673-5677 (1989); Pang et al., *Biotechniques*, 22:1046-1048 (1977); Huang et al., *Methods Mol. Biol.*, 69:89-96 (1997); Huang et al., *Method Mol. Biol.*, 67:287-294 (1997); Benkel et al., *Genet. Anal.*, 13:123-127 (1996); Hartl et al., *Methods Mol. Biol.*, 58:293-301 (1996)). The term "chromosome walking" means a process of extending a genetic map by successive hybridization steps.

The nucleic acid molecules of the present invention may be used to isolate promoters of cell-enhanced, cell-specific, tissue-enhanced, tissue-specific, developmentally- or environmentally-regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (see, for example, Birren et al., *Genome Analysis: Analyzing DNA*, 1 (1997), Cold Spring Harbor Laboratory Press, Cold Spring Harbor, N.Y.). Promoters obtained utilizing the nucleic acid molecules of the present invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the present invention includes nucleic acid molecules that are markers. The markers can be used in a number of conventional ways in the field of molecular genetics. Such markers include nucleic acid molecules SEQ ID NOs: 11, 12, 13, 16, 17, 19, 21, 23, 25, and 27, and complements thereof, and fragments of either that can act as markers and other nucleic acid molecules of the present invention that can act as markers.

In an aspect of the present invention, one or more of the nucleic molecules of the present invention are used to determine the level (i.e., the concentration of mRNA in a sample, etc.) in a plant (preferably canola, corn, *Brassica campestris*, oilseed rape, rapeseed, soybean, crambe, mustard, castor bean, peanut, sesame, cottonseed, linseed, safflower, oil palm, flax, or sunflower) or pattern (i.e., the kinetics of expression, rate of decomposition, stability profile, etc.) of the expression of a protein encoded in part or whole by one or more of the nucleic acid molecule of the present invention.

A number of methods can be used to compare the expression between two or more samples of cells or tissue. These methods include hybridization assays, such as Northerns, RNAse protection assays, and in situ hybridization. Alternatively, the methods include PCR-type assays. In a preferred method, the expression is compared by hybridizing nucleic acids from the two or more samples to an array of nucleic acids. The array contains a plurality of suspected sequences known or suspected of being present in the cells or tissue of the samples.

The present invention now being generally described, it will be more readily understood by reference to the following examples, which are included for purposes of illustration only and are not intended to limit the present invention.

EXAMPLES

Example 1

Isolation of DGAT2 Nucleic Acid Sequences and Confirmation of DGAT Activity.

*Mortierella ramanniana* was cultured as described by Kamisaka, Y. et al., *Lipids*, 28:583-587 (1993). Cells were harvested by passing 10-13 day old cultures through Miracloth and removing excess liquid by hand-wringing. Wet packed cells were stored at −70° C. Purification of DGAT2 proteins from *Mortierella ramanniana* was performed as follows. Lipid bodies were isolated from 70-75 g of wet packed cells. Immediately prior to use, cells were thawed on ice and resuspended in 200 mL of Buffer D (10 mM potassium phosphate (pH 7.0), 1 M KCl, 0.5 M sucrose, 1 mM EDTA). Samples were lysed with an equal volume of 0.5 mm glass beads in a cell disrupter (Bead-Beater, Biospec Products, Bartlesville, Okla.) set on 'Homogenize' for 45-90 seconds. The cell slurry containing glass beads was centrifuged at 500×g, the supernatant was removed, and the pellets were washed with another 5 mL of Buffer D. Following centrifugation, the supernatants from both centrifugations were combined. It was divided into six ultracentrifuge tubes (25×89 mm) and each was overlaid with 5 mL of Buffer E (10 mM potassium phosphate, pH 7.0, 1 M KCl, and 0.3 M sucrose). Samples were centrifuged at 100,000×g at 4° C. for 3 hours.

The lipid body fractions, floating on top of the overlays, were combined and solubilized in 50 mL of Buffer F (10 mM potassium phosphate (pH 7.0), 75 mM KCl, 0.5 M Sucrose and 1.5% Triton X-100). Non-solubilized material was removed by ultracentrifugation (90,000×g for 1.8 hours). The floating lipid layer was discarded and the supernatant containing the solubilized fraction (Triton X-100 extract) was retained for column purification. DGAT activity was measured as the production of $^{14}C$ triacylglycerol from $[1-^{14}C]$ oleoyl-CoA and unlabeled dioleoyl-DAG. For non-solubilized samples the reaction mixture (0.1 mL) consisted of enzyme extract, 3.67 μM $[1-^{14}C]$oleoyl-CoA, and 1.5 mM 1,2-18:1 diacylglycerol in a buffer containing 10 mM potassium phosphate (pH 7.0), 100-150 mM KCl, and 0.1% Triton x-100 (w/v). Assay mixtures were incubated at 25° C. for 5 minutes and reactions were terminated by adding 1.5 mL of heptane:isopropanol:0.5 M $H_2SO_4$ (10:40:1, v/v/v). For solubilized samples 1,2-18:1 DAG was reduced to 0.5 mM, Triton X-100 was increased to 0.2%, and 300 μM L-α-phosphatidic acid was included. The L-α-phosphatidic acid was required to recover activity following solubilization with detergent as described by Kamiska et al., *J. Biochem.*, 119:520-523 (1996) except, 300 μM phosphatidic acid was used rather than 500 μM. This resulted in a greater stimulation of activity.

Following solubilization, product formation was dependent on the addition of exogenous DAG. Under these conditions the reaction rate was linear with respect to time for up to 10 minutes. After the assay was stopped, radiolabeled glycerolipids were isolated by adding 0.1 mL of 1 M $NaHCO_3$ and 1 mL of heptane containing 15 nmoles/mL triolein as a carrier. The mixture was vortexed and the upper organic phase was removed to a new glass vial. The organic extract was back-extracted with 1 mL of 1 M NaCl. Forty percent of the final organic phase was removed for liquid scintillation counting and the remaining organic phase evaporated to dryness under nitrogen gas. The residue was resuspended in hexane and subjected to TLC on silica gel-G with a preadsorbent loading zone (Analtech #31011, Newark, Del.). The TLC plate was developed in hexane:diethyl ether:acetic acid (50:50:1, v/v/v), before drying and scanning by a radio-image analyzer (AMBIS 3000, AMBIS, Inc., San Diego, Calif.) to determine the portion of radioactivity incorporated into TAG. Confirmation of TAG activity on the TLC plate was determined by co-migration of the unlabeled triolein carrier and the [$^{14}C$]TAG following exposure to iodine vapor.

DGAT activity in the Triton X-100 extract was further purified by dye-binding chromatography on a Yellow 86-Agarose column (2.5 cm×6.4 cm) equilibrated with 75 mM KCl in Buffer G (10 mM potassium phosphate (pH 7.0), 0.1% (w/v) Triton X-100, 10% (w/v) glycerol). The column was washed with 5 volumes of equilibration buffer at 2 mL per minute, then the activity was eluted with 500 mM KCl in Buffer G. DGAT activity is stable to freeze/thaw at this stage of purification, so eluted fractions were assayed immediately and active fractions were stored at −70° C. In order to maintain maximal activity, subsequent chromatography was performed and fractions were assayed on the same day. Four preparations of Yellow 86-Agarose-purified activity were combined and concentrated 12-fold by ultrafiltration (YM-30 membrane, Amicon, Beverly, Mass.). The activity was further purified by hydroxyapatite chromatography on a 1.0 cm×25.5 cm column equilibrated with 500 mM KCl in Buffer G. The column was washed with 40 mL of equilibration buffer before bound proteins were eluted with a step gradient to 100 mM di-potassium phosphate in the equilibration buffer. Fractions from the flow-through containing DGAT activity were pooled and diluted 1:3.3 in Buffer G to reduce the KCl concentration from 500 to 150 mM. The diluted sample was applied to a heparin column CL-6B (0.55×4.7 cm) equilibrated with 150 mM KCl in Buffer G. The column was washed with 5 volumes of equilibration buffer at 0.5 mL/minute and bound proteins were eluted in a 10 mL linear gradient of 150-500 mM KCl followed by 10 mL of 500 mM KCl in Buffer G at 0.25 mL/minute. Fractions of 1.1 mL were collected. Two activity peaks were eluted from the heparin column (fnx 22 and fxn 28).

A summary of the protein purification scheme is shown in Table 1. A lipid body fraction isolated from 300 g of *M. ramanniana* cell paste was used for the preparation. Recovery values for Mr-DGAT2A (Heparin fxn 28) and Mr-DGAT2B (Heparin fxn 22) are reported separately in the last chromatographic step.

TABLE 1

| | Purification scheme for DGAT2 | | | | |
|---|---|---|---|---|---|
| Fraction | Protein (mg) | Activity (nmol/min) | Specific Act. (nmol/min/mg) | Fold Purification | Recovery (%) |
| 500 g | 2341.2 | 1218.0 | 0.5 | 1.0 | 100 |
| Tx-100 extract | 117.6 | 2069.2 | 17.6 | 33.8 | 169.8 |
| Yellow load | 63.6 | 1458.8 | 22.9 | 44.1 | 119.7 |
| Yellow Ft/wash | nd | 719.2 | nd | nd | 59.0 |
| Yellow eluted | 1.6 | 678.0 | 440.3 | 846.2 | 55.7 |
| HA pool | 0.56 | 340.2 | 607.6 | 1167.6 | 27.9 |
| Heparin eluted | 0.20 | 264.6 | 1323.0 | 2646.0 | 21.7 |
| Heparin fxn 22 | 0.0026 | 51.0 | 1961.5 | 3769.5 | 4.2 |
| Heparin fxn 28 | 0.0076 | 20.0 | 2631.6 | 5057.2 | 1.6 |

Polyacrylamide gradient gel electrophoresis (10-13%) was carried out according to the method of Laemmli, *Nature*, 227680-227685 (1970) with some of the modifications of Delepelaire, *Proc. Nat. Acad. Sci.*, 76:115-115 (1979). The resolving gel contained a 10-13% linear gradient of acrylamide stock stabilized by a 0-10% linear gradient of sucrose. Proteins were visualized by staining with silver according to the method of Blum et al., *Electrophoresis*, 8:93-99 (1987), or with Coomassie Blue (0.1% Coomassie Blue R-250, 50% methanol (v/v), 10% acetic acid (v/v)).

Several protein bands (36.5 kD, 36 kD, 35 kD, and 34 kD) were associated with the first peak of activity (fxn 22). The 34 kD band did not correlate with DGAT activity in all chromatographic steps, so it was eliminated (i.e., data not shown). The second peak (fxn 28) had a higher specific activity (Table 2) and contained a major protein band at 36 kD by SDS- PAGE. Three proteins (36.5 kD, 36 kD, and 35 kD) were identified from the purification as potential DGAT candidates.

Degenerate primers designed from the amino acid sequences generated from the 36 kD peptide, were constructed in both sense and antisense orientations. These primers were employed in different combinations to amplify cDNA produced from *Mortierella ramanniana* total RNA. Total RNA was prepared from wet packed cells essentially as described by Jones et al., *The Plant Cell*, 7:359-371 (1995). cDNA was synthesized from the RNA using the Marathon cDNA Amplification Kit (BD Biosciences Clontech, Inc. Palo Alto, Calif.). The amplification mixture consisted of template, polymerase chain reaction buffer, 200-300 ng of each primer, 2.5 mM dNTP, and 1 unit of AmpliTaq Gold polymerase (Perkin Elmer, Norwalk, Conn.) in 50 µL. The amplification program consisted of one 10-minute hold at 95° C., and 30 cycles of denaturation (94° C., 30 seconds), annealing (62° C., 10 seconds, 10% ramp to 50° C., 15 seconds), and primer extension (72° C., 2 minutes). Products of the reaction were separated on a 0.7% agarose gel, excised, and purified according to the QIAPREP DNA extraction handbook (Qiagen, Santa Clara, Calif.). The purified products were cloned into the pCR2.1TOPO vector (Invitrogen, Carlsbad, Calif.) and analyzed by DNA sequencing. Comparisons between peptide sequences obtained by Edman degradation that were not used to design the primers and the deduced amino acid sequences of PCR products were used to confirm the identity of the fragments.

Figure 1C:
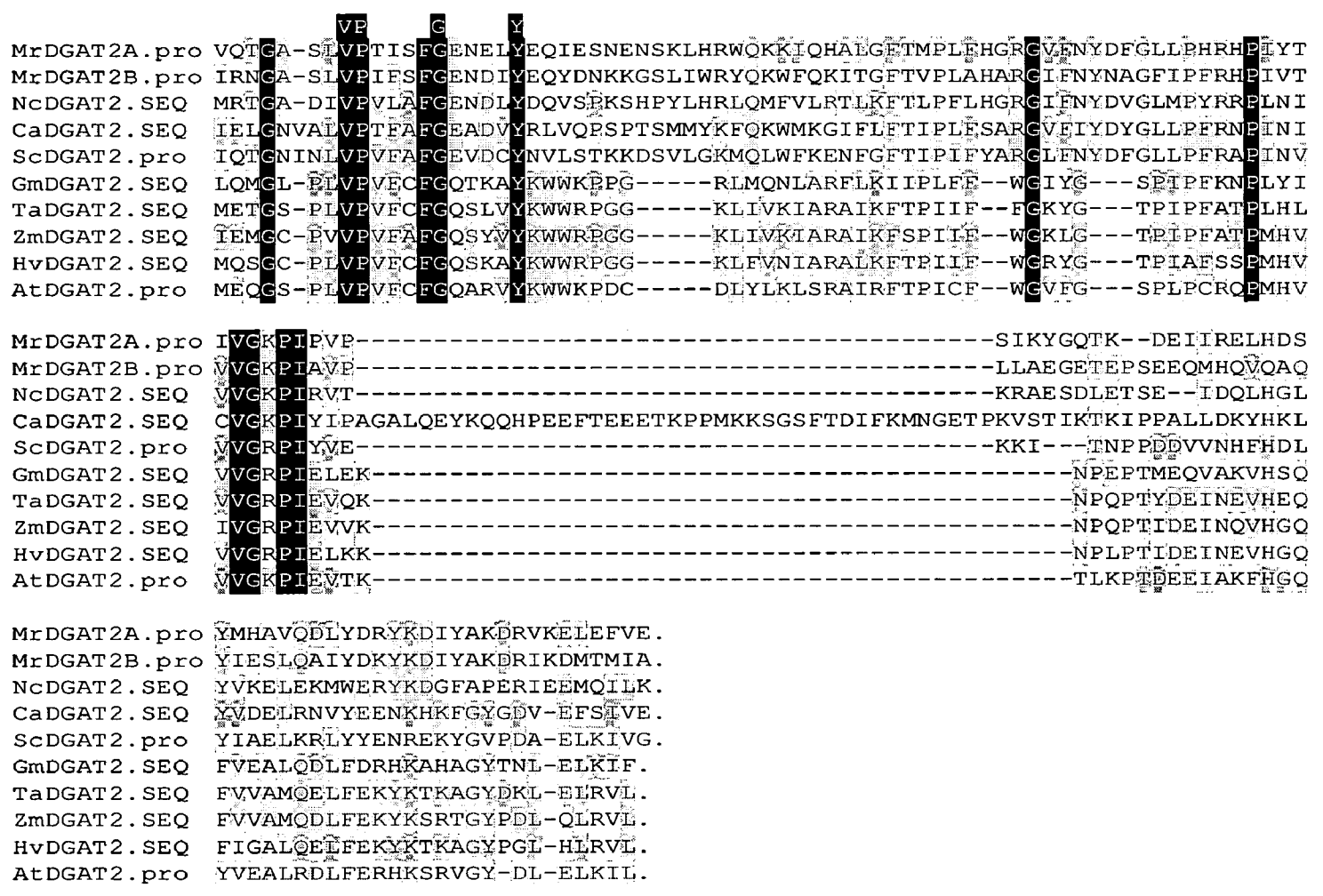

RACE reactions (Marathon cDNA Amplification Kit) using primers specific to these fragments were performed to yield a 1312 base pair (bp) long cDNA that was cloned into the pCR2.1-TOPO vector. The most 5' ATG codon of this reading frame was located at bp 76, allowing for the translation of a polypeptide of 355 amino acids in length (FIG. 1, MrDGAT2A).

Genbank searches showed that these polypeptides are not sequence-related to the known DGAT1 or any other acyl transferases, but are members of a previously unannotated gene family present in major phyla of eukaryotes, in particular fungi, plants, animal, and basal eukaryotes.

The commercial BAC-to-BAC Baculovirus Expression System (Life Technologies, Inc., Gaithersburg, Md.) was used to express full-length proteins of *Mortierella ramanniana* DGAT2A and DGAT2B in cultured insect (sf9) cells. Full-length DGAT2 open reading frames were amplified by PCR employing primers containing restriction sites at the 5' ends (NotI and SpeI to the sense primers and PstI to the antisense primers). The PCR products were cloned into the pCR2.1TOPO vector and sequenced to confirm the fidelity of the constructs. Full-length cDNAs in pCR2.1-TOPO vectors were digested with NotI and PstI and cloned into the NotI and PstI restriction sites of the pFASTBAC1 vector (Life Technologies, Inc.). The baculovirus expression system can be used to express the full length cDNA encoding the polypeptides that are set forth in SEQ ID NOs: 18, 20, 22, 24, 26, and 28 to determine DGAT activity.

Insect cells ($1 \times 10^6$ cells/mL) were infected at a multiplicity of infection (MOI) of 0.05-0.1 and harvested after 5 days at 27° C. by centrifugation. Pelleted cells were re-suspended in Buffer H (100 mM Tricine-NaOH, pH 7.8, 10% glycerol, 100 mM NaCl) and lysed by sonication (2×10 seconds). Cell walls and other debris were pelleted by centrifugation and discarded. Membranes were harvested by centrifugation of the supernatant fraction (100,000×g for one hour) and pellets were resuspended in Buffer H for enzyme assay. DGAT activity in insect cell membranes was measured as the production of $^{14}C$ triacylglycerol from $[1-^{14}C]$ oleoyl-CoA and unlabeled dioleoyl-DAG. The reaction mixture (0.1 mL) consisted of isolated membranes, 3.5 µM $[1-^{14}C]$oleoyl-CoA, 21.5 µM oleoyl-CoA and 200 µM 1,2-18:1 diacylglycerol in a buffer containing 25-30 mM Tricine (pH 7.8), 50-60 mM NaCl, and 0.06% CHAPS (w/v). Assay mixtures were incubated at 25° C. for 5-10 minutes and reactions were terminated by adding 1.5 mL of heptane:isopropanol:0.5 M $H_2SO_4$ (10:40:1, v/v/v). Samples were processed as described above. Assays were linear with respect to protein and time.

A significant elevation in DGAT activity was detected relative to untransformed sf9 cells for both *Mortierella ramanniana* DGAT2A (94-fold) and DGAT2B proteins (37-fold) (Table 2).

TABLE 2

| Sample<br>Insect Cell Membranes | DGAT Activity<br>pmol/min/mg |
| --- | --- |
| Control | 1299.7 |
| MrDGAT2A | 122182.1 |
| MrDGAT2B | 48146.0 |

Enzymological properties of the expressed *Mortierella ramanniana* DGAT2A and DGAT2B genes were also investigated. The effect of pH on DGAT activity was evaluated over a range of 4.0 to 11.0. The pH optimum for both enzymes was observed at 6.8. No differences were detected between the two polypeptides with respect to pH. A difference was observed in their response to temperature. The temperature optimum for DGAT2A was 37° C. whereas DGAT2B does not demonstrate an optimum temperature Example 2

Isolation of *Neurospora crassa* DGAT2 Nucleic Acid Sequence and Confirmation of DGAT Activity.

The following protocol was used to obtain the entire coding region corresponding to the *Neurospora crassa* DGAT2 protein (NcDGAT2). RNA was isolated from *Neurospora crassa* mating type A (Fungal Genetics Stock Center, Kansas City, Kans.) mycelium using Tri-Reagent (Sigma, St. Louis, Mo.) according to the manufacturer's protocol. First-strand cDNA synthesis was completed using the SMART cDNA Amplification kit (Clontech, California). Based on sequence comparisons to the *Neurospora crassa* genomic sequences, gene specific primers were designed to amplify the full-length coding regions of the NcDGAT2 sequence. Additional restriction sites were introduced to facilitate cloning (HindIII and RsrII), using the primers designated SEQ ID NO: 7 and SEQ ID NO: 8 (FIG. 3). The PCR product was cloned into plasmid pCR2.1 according to the manufacturer's protocol (Invitrogen) to yield plasmid pMON69834. Double-stranded DNA sequencing was done to verify the sequence (SEQ ID NO: 13). For expression of the NcDGAT2 protein in insect cells using a baculovirus expression system, the RsrII -HindIII fragment of pMON69834 was cloned into RsrII-HindIII-digested plasmid pFASTBAC1 (Gibco-BRL, Gaithersburg, Md.). The resulting plasmid, pMON69839, was transformed into *E. coli* DH10BAC and the protein was expressed using the BAC-to-BAC Baculovirus Expression System (Gibco-BRL) according to the manufacturers directions, excepting that harvesting of recombinant viruses was done 5 days post-transfection. The supernatant from the transfection mixture was used for generating virus stock, which in turn was used for infecting Sf9 cells for use in the assay. DGAT activity was measured as the production of $^{14}C$ triacylglycerol from [1-$^{14}C$]oleoyl-CoA and unlabeled dioleoyl-DAG. The reaction mixture (0.1 mL) consisted of isolated membranes, 3.5 µM [1-$^{14}C$]oleoyl-CoA, 21.5 µM oleoyl-CoA and 200 µM 1,2-18:1 diacylglycerol in a buffer containing 25-30 mM Tricine (pH 7.8), 50-60 mM NaCl, and 0.06% CHAPS (w/v). Assay mixtures were incubated at 25° C. for 5-10 minutes and reactions were terminated by adding 1.5 mL of heptane:isopropanol:0.5 M $H_2SO_4$ (10:40:1, v/v/v). Samples were processed as described in Example 1. DGAT activity was increased 6-fold in the cells transformed with plasmid pMON69839 relative to activity in untransformed (sf9) cells.

For expression of the NcDGAT2 sequence in plants, the gene was PCR amplified from pMON69834 in order to introduce NotI and Sse8387I cloning sites using primers oligoDB#19911 (SEQ ID NO: 9) and oligoDB#19912 (SEQ ID NO: 10) (FIG. 3). The PCR product was digested with NotI-Sse8387I and the 1071 bp fragment was ligated with the NotI-Sse8387I-digested vector from pMON67164 to form pMON68762. In this plasmid the gene is under control of a napin promoter. Plasmid pMON68762 was introduced into *Agrobacterium tumefaciens* ABI strain, which was used to transform soybean as described in Martinell et al., U.S. Pat. No. 6,384,301.

Example 3

Preparation and Transformation of Resynthesized DGAT2 Genes

A codon usage table was constructed from 8 highly expressed seed specific proteins from soybean namely conglycinin (GenBank Accession #AB008678, AB008679, AB008680), glycinin (AB003680, AB004062), and globulin (D16107, U59425), and 14 highly expressed seed specific proteins from canola namely cuciferin, (GenBank Accession # 167133, 167135, 17800, 17804, 17810, 21117), and napin (AA349403, 167176, 167178, 167174, 167154, 17836, 17834, 17832). The MrDGAT2B and ScDGAT2 amino acid sequences (SEQ ID NO: 4 and SEQ ID NO: 6, respectively), along with the codon usage table described above, were sent to Blue Heron Biotechnology Inc., (Bothell, Wash.), who then utilized a proprietary algorithm to generate the final codon-optimized nucleotide sequence with the lowest free energy-of-forming RNA secondary structures. The codon-optimized sequence of MrDGAT2B was synthesized by Blue Heron Biotechnology, Inc., and named MrDGAT2B.nno (SEQ ID NO: 11). The codon-optimized sequence of ScDGAT2 was synthesized by Midland Certified Reagent Company (Midland, Tex.) and named ScDGAT2.nno (SEQ ID NO: 16).

Plasmid pMON70924, containing MrDGAT2B.nno in an *E. coli* expression vector, was sequenced to confirm DNA as reported by Blue Heron Biotechnology. Plasmid DNA was digested with XhoI and filled to make a blunt end and then was digested with Sse8387I. The 1068 bp fragment was ligated with the blunt/Sse8387I-digested vector pMON70918 to form pMON70925. In this plasmid the gene is under control of a napin promoter.

Plasmid pMON70917, containing ScDGAT2.nno, was sequenced to confirm DNA as reported by Midland Certified Reagent Company. Plasmid DNA was digested with NotI-Sse8387I and the 1269 bp fragment was gel purified. The fragment was ligated to NotI-Sse8387I-digested pMON70918 to form pMON70920. In this plasmid the gene is under control of a napin promoter. ScDGAT2.nno was cloned into another expression vector, using similar techniques, so that the gene was expressed under control of the USP88 promoter (pMON70923). Plasmids pMON70925, pMON70923, and pMON70920 were introduced into *Agrobacterium tumefaciens* ABI strain, and each were used to transform soybean as described in Martinell et al., U.S. Pat. No. 6,384,301.

Similarly, the NcDGAT2 amino acid sequence (SEQ ID NO: 14) and the codon usage table described above were sent to Blue Heron Biotechnology, Inc., where a codon-optimized nucleotide sequence with the lowest free energy-of-forming RNA secondary structures was generated. The codon-optimized sequence of NcDGAT2 is synthesized by Blue Heron Technology and is named NcDGAT2.nno (SEQ ID NO: 12). The resynthesized NcDGAT2.nno is sequenced to confirm DNA as reported by Blue Heron Biotechnology. Plasmid DNA is digested with NotI-Sse8387I and the fragment is gel purified. The fragment is ligated to NotI-Sse8387I digested pMON67164 to create a plasmid where the gene is under control of a napin promoter.

Vectors are constructed that express a sequence set forth in SEQ ID NOs: 17, 19, 21, and 23, in the genome of a plant host to obtain transcription or transcription and translation of the sequence to effect phenotypic change. Transgenic soybean plants can be obtained by Agrobacterium-mediated transformation as described by Martinell et al., U.S. Pat. No. 6,384,301.

Example 4

Expression of DGAT2 in Plants

A resynthesized *Mortierella ramanniana* DGAT2A gene, MrDGAT2A.nno, (SEQ ID NO: 15) was expressed in soybean under control of soybean 7S promoter sequence (pCGN8832). Plants were transformed by particle bombardment and enzyme assays were performed on pooled, developing $R_1$ seed. Several plants exhibited significant increases (5-20 fold, Students t Test, alpha=0.05) in DGAT activity relative to untransformed plants and are shown in Table 3.

TABLE 3

| Sample pCGN8832 R1 Developing seed pools | DGAT Activity pmol/min/mg |
| --- | --- |
| Control 1 | 37.4 |
| Control 2 | 146.7 |
| 8832-13 | 27.0 |
| 8832-9 | 40.4 |
| 8832-2 | 55.1 |
| 8832-12 | 57.4 |
| 8832-1 | 92.9 |
| 8832-7 | 96.1 |
| 8832-6 | 111.2 |
| 8832-17 | 115.2 |
| 8832-3 | 134.6 |
| 8832-5 | 183.0 |
| 8832-15 | 188.1 |
| 8832-16 | 190.9 |
| 8832-8 | 561.5 |
| 8832-11 | 672.0 |
| 8832-4 | 709.5 |
| 8832-10 | 741.5 |
| 8832-14 | 901.3 |

DGAT activity in plants was assayed as follows. Developing embryos were ground in liquid nitrogen using a mortar and pestle. A portion of the sample was reconstituted with Tricine buffer (100 mM Tricine, pH7.5, 280 mM NaCl, 10% glycerol) and protein concentration was determined by Bradford reagent (Sambrook et al., *Molecular Cloning, A Laboratory Manual, 2nd Ed., Cold Spring Harbor Press,*

Cold Spring Harbor, N.Y., 1989). Samples were diluted to 1 mg/ml and 10 μl were used in the assay. DGAT activity was measured as the production of $^{14}C$ triacylglycerol from [1-$^{14}C$]oleoyl-CoA and unlabeled dioleoyl-DAG. The reaction mixture (0.1 mL) consisted of protein homogenates, 3.5 μM [1-$^{14}C$]oleoyl-CoA, 10 μM oleoyl-CoA and 1.5 mM 1,2-18:1 diacylglycerol in a buffer containing 25 mM Tricine (pH 7.8), 28 mM NaCl, and 0.06% CHAPS (w/v). Assay mixtures were incubated at 25° C. for 10 minutes and reactions were terminated by adding 1.5 mL of heptane:isopropanol:0.5 M $H_2SO_4$ (10:40:1, v/v/v). Samples were processed as described in Example 1.

$R_1$ seed from plants expressing the MrDGAT2A.nno gene were advanced to the next generation ($R_2$). Oil and protein levels were determined by Near-Infra-Red (NIR) analysis of mature $R_2$ seed. NIR spectra of pooled seed samples harvested from individual plants are measured, and oil levels are calculated based on regression analysis using a standard curve generated from analysis of soybean seed with varying oil levels as determined gravimetrically following accelerated solvent extraction (*Better Solutions for Food and Beverage Analysis, 2nd Edition,* Dionex Corporation, Sunnyvale, Calif. (1997)). A statistically significant increase of 1.7% was observed between the oil mean of seeds homozygous for MrDGAT2A.nno compared to the oil mean of seeds that did not contain the transgene (nulls) (Students T test, alpha=0.05). A statistical evaluation of the protein data showed there was no difference in the means (Students T test, alpha=0.05).

For expression of the resynthesized MrDGAT2A sequence in plants under the control of the napin promoter, the NotI-Sse 8387I fragment was ligated with the NotI-Sse8387I-digested binary vector pMON67164 to yield plasmid pMON70904. Plasmid pMON70904 was introduced into the *Agrobacterium tumefaciens* ABI strain, which was then used to transform soybean. Developing R1 seed was harvested from the R0 plant and assayed for DGAT activity. A selected number of events with elevated activity were advanced one generation (R2 seed). Oil levels and protein levels in mature second generation seed were determined by Near Infrared Transmittance (NIT) spectroscopy, whereby NIT spectra of pooled seed samples harvested from individual plants are measured, and oil and protein levels are calculated based on regression analysis using a standard curve generated from analysis of soybean seed with varying oil or protein levels, as determined gravimetrically following accelerated solvent extraction or elemental (% N) analysis, respectively. A statistically significant increase of 2.6% was observed between the oil mean of seeds homozygous for MrDGAT2A.nno compared to the oil mean of seeds that did not contain the transgene (nulls) (Students t Test, alpha=0.05). A statistical evaluation of the protein data showed there was no difference in the means (Students t Test, alpha=0.05).

Example 5

Expression of DGAT2 from Multiple Promoters

Two proteins exhibiting DGAT2 activity were identified in *Mortierella ramanniana* (MrDGAT2A and MrDGAT2B). To construct a plasmid capable of expressing two DGAT genes, 2 genes were cloned into the same plasmid on a single t-DNA. Plasmid pMON70927 contained MrDGAT2A.nno (SEQ ID NO: 15) under control of the 7Sa' promotor and MrDGAT2B.nno (SEQ ID NO: 11) under control of the napin promoter. The cloning was as follows: pMON70900, containing MrDGAT2A.nno under control of the 7Sa' promoter, was digested with EcoRV and filled to make blunt ends. The DNA was then cut with NotI and the 7Sa':MrDGAT2A.nno fragment was gel purified. The fragment was ligated to the blunt/NotI-digested plant expression vector pMON63689 to form pMON70912. To obtain MrDGAT2B.nno, pMON70924 was digested with XhoI and EcoRI and the ends were filled to create a blunt/blunt fragment that was 1071 bp long. The fragment was gel purified and then ligated to blunt/blunt pCGN7770 (an *E. coli* expression vector containing the napin promoter and 3' UTR) to form pMON70926. This plasmid containing MrDGAT2B.nno in the napin expression cassette was digested with NotI and the fragment was ligated to NotI-digested pMON70912, described above, to form pMON70927. pMON70927 was introduced into *A. tumefaciens* ABI strain, which was used to transform soybean as described in Martinell et al., U.S. Pat. No. 6,384,301.

Other DGAT2 genes, including, but not limited to, MrDGAT2A (SEQ ID NO: 1), MrDGAT2B (SEQ ID NO: 3), ScDAGT2 (SEQ ID NO: 5), NcDGAT2 (SEQ ID NO: 13), NcDGAT2,nno (SEQ ID NO: 12), and ScDGAT2.nno (SEQ ID NO: 16) are cloned in a similar manner, either in pairs or in duplicate. The promoters that are used control the expression with respect to time and/or strength.

Example 6

Expression of MrDGAT2A in Corn Germ

Figure 6:
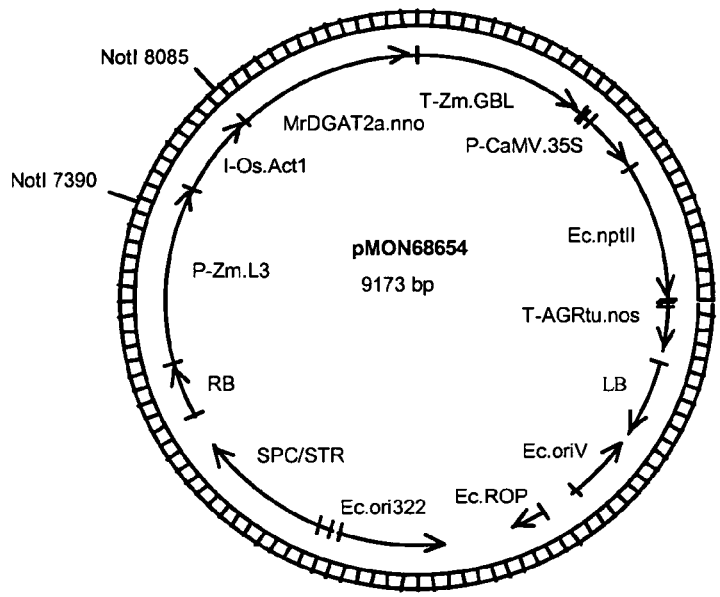
FIG. 6 is a schematic of vector pMON68654.
Figure 7:
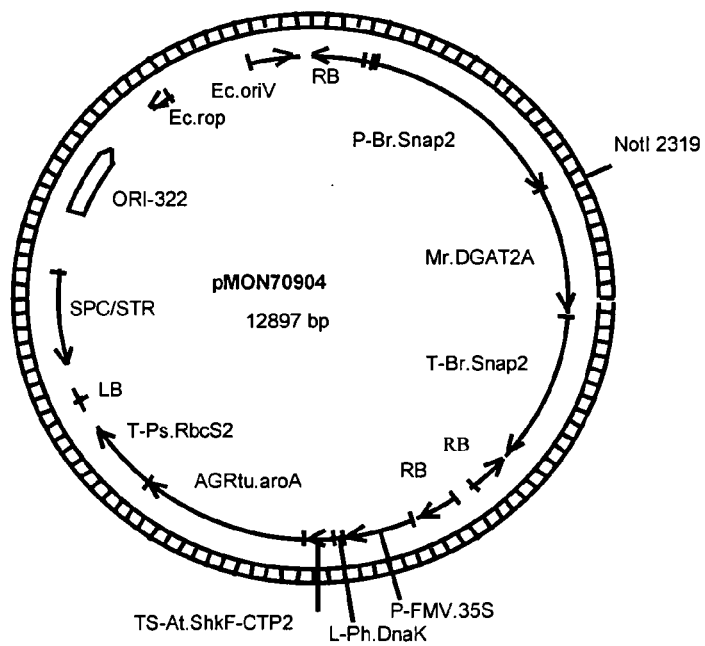
FIG. 7 is a schematic of vector pMON70904.
Figure 8:
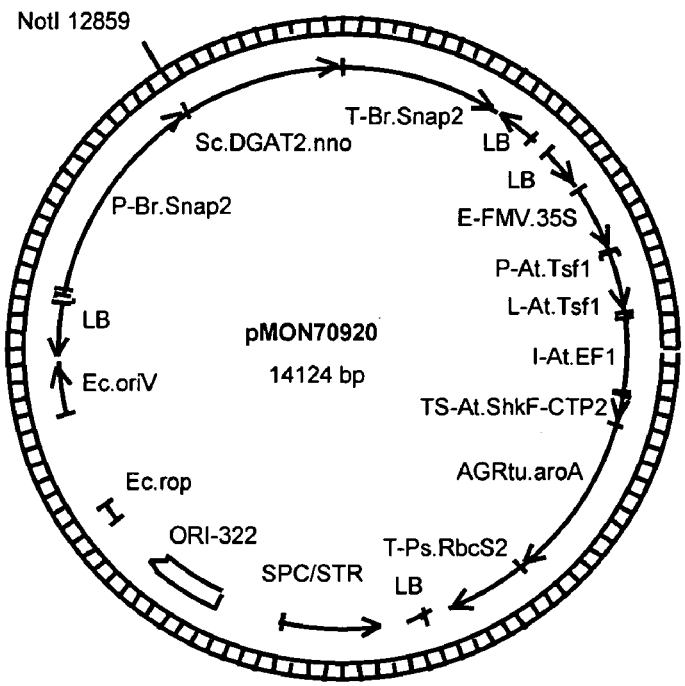
FIG. 8 is a schematic of vector pMON70920.
Figure 9:
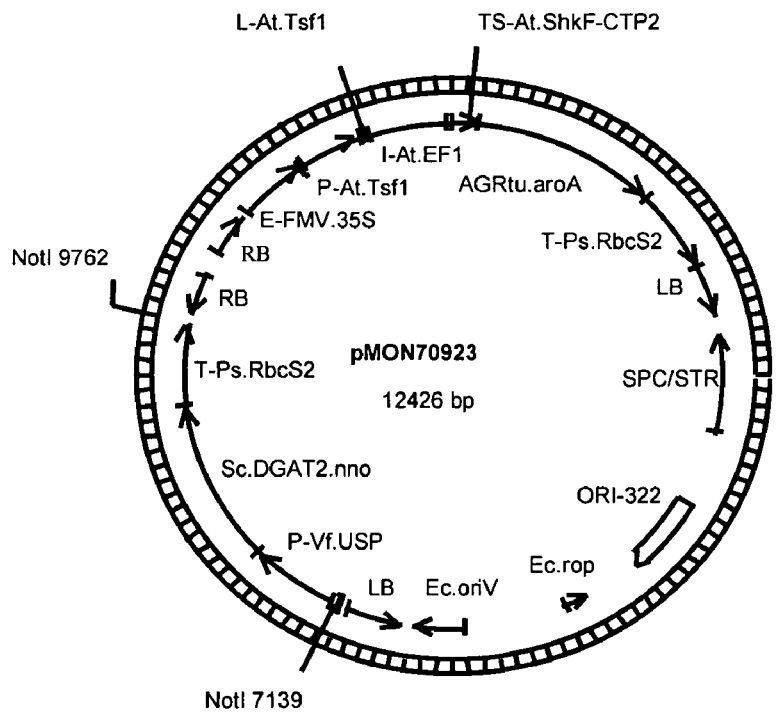
FIG. 9 is a schematic of vector pMON70923.
Figure 10:
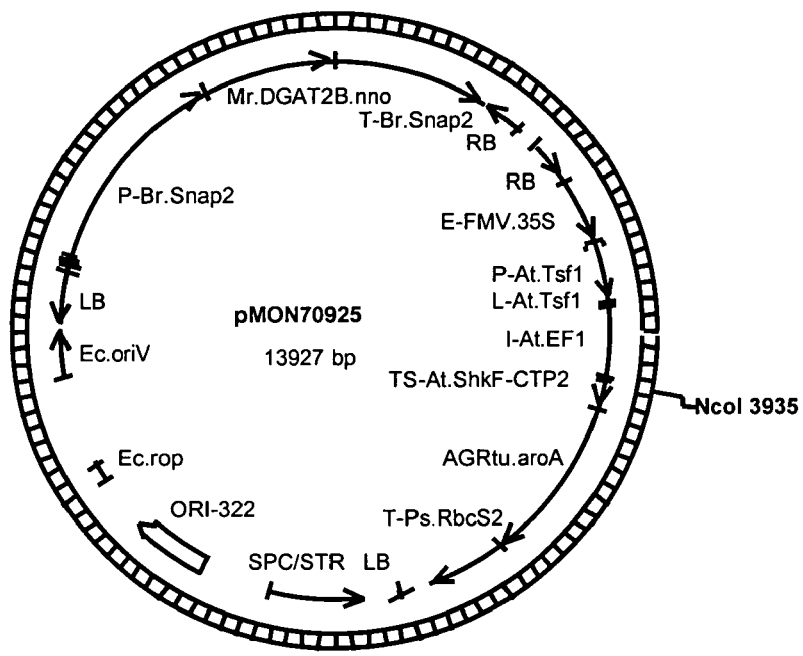
FIG. 10 is a schematic of vector pMON70925.
Figure 11:
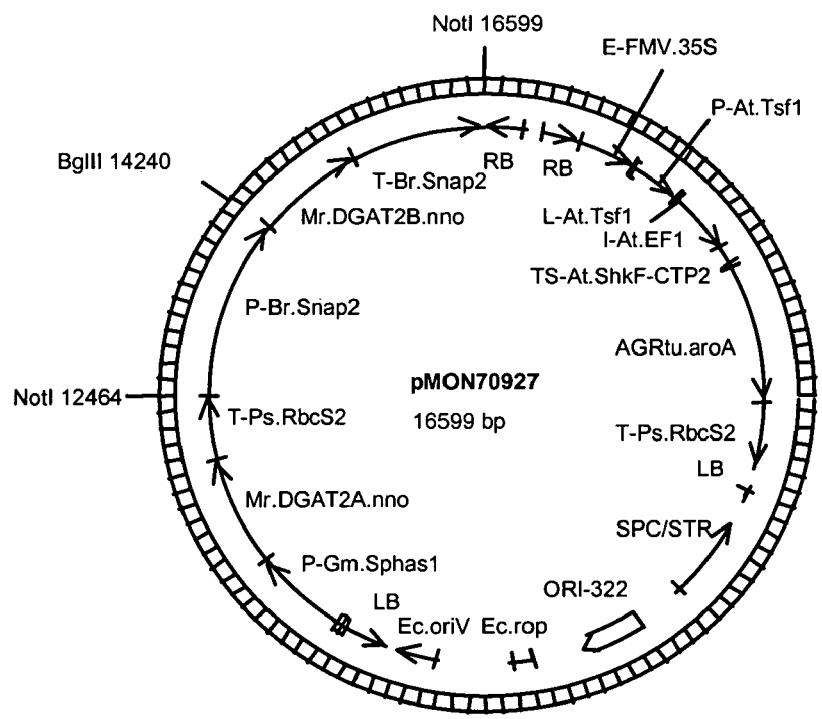
FIG. 11 is a schematic of vector pMON70927.

An expression vector was prepared to engineer germ-targeted expression of the resynthesized *Mortierella ramanniana* DGAT2A (SEQ ID NO: 15) gene in corn. Specifically, the full length MrDGAT2A.nno gene (SEQ ID NO: 15) contained in a 1076 base pair Not 1/Sse8387I fragment was cloned into the Bsp120I/Sse8387I sites of pMON72021 directly 3' of the *Zea mays* L3 oleosin promoter followed by the rice actin intron and 5' of the globulin 1 3'UTR to produce pMON68654 (FIG. 6).

The construct pMON68654 was transformed into the elite maize line LH59 by *Agrobacterium tumefaciens* ABI-mediated transformation. Events resulting from this transformation demonstrate an increase in oil.

What is claimed is:

1. An isolated nucleic acid molecule comprising a nucleic acid sequence encoding a polypeptide having diacylglycerol acyltransferase activity, wherein the nucleic acid molecule is selected from the group consisting of (a) a nucleic acid sequence that encodes a polypeptide comprising a sequence that is at least 95% identical to SEQ ID NO: 14; and (b) a nucleic acid sequence comprising a sequence that is at least 90% identical to SEQ ID NO: 12 or SEQ ID NO: 13.

2. The isolated nucleic acid molecule of claim 1, wherein the polypeptide comprises the sequence of SEQ ID NO: 14.

3. The isolated nucleic acid molecule of claim 1, defined as comprising the nucleic acid sequence of SEQ ID NO: 12.

4. The isolated nucleic acid molecule of claim 1, wherein the nucleic acid sequence comprises of SEQ ID NO: 13.

5. A DNA construct comprising an expression cassette comprising a heterologous promoter that functions in a plant cell operably linked to a nucleic acid molecule of claim 1.

6. The DNA construct of claim 5, further comprising a second expression cassette wherein said second expression cassette comprises a second heterologous promoter that functions in a plant cell operably linked to a nucleic acid that encodes a polypeptide for a diacylglycerol acyltransferase.

7. A plant or seed comprising the DNA construct of claim 5.

8. The plant or seed of claim 7, wherein the plant or seed is selected from the group consisting of maize, soybean, canola, oil seed rape, cotton, sesame, flax, peanut, sunflower, safflower, olive, and oil palm.

9. The plant or seed of claim 7, wherein the plant or seed is used to produce a product.

10. The plant or seed of claim 9, wherein the plant or seed is used to produce a product selected from the group consisting of feed, meal, oil, and protein.

11. A plant or seed comprising the DNA construct of claim 6.

12. The plant or seed of claim 11, wherein the plant or seed is selected from the group consisting of maize, soybean, canola, oil seed rape, cotton, sesame, flax, peanut, sunflower, safflower, olive, and oil palm.

13. The plant or seed of claim 11, wherein the plant or seed is used to produce a product.

14. The plant or seed of claim 13, wherein the plant or seed is used to produce a product selected from the group consisting of feed, meal, oil, and protein.

15. A method of producing a plant comprising the steps of: (A) transforming a plant cell with a DNA construct of claim 6; and, (B) regenerating said plant cell into a fertile plant, wherein seeds of the fertile plant comprising the construct have increased oil yield or altered oil composition relative to seed from a plant having the same genetic background but lacking the DNA construct.

16. The method of claim 15, wherein said plant provides seed having an increased oil yield relative to seed from a plant having the same genetic background but lacking the DNA construct.

17. The isolated nucleic acid molecule of claim 1, wherein the nucleic acid molecule encodes a polypeptide having at least one amino acid motif selected from the group consisting of: AYVFGYEPHSVXPI (SEQ ID: 33) and FXXPXYR (SEQ ID NO: 34).

18. The isolated nucleic acid molecule of claim 1, wherein the nucleic acid sequence encodes a polypeptide comprising a sequence that is at least 95% identical to SEQ ID NO: 14.

19. The isolated nucleic acid molecule of claim 1, wherein the nucleic acid sequence encodes a polypeptide comprising a sequence that is at least 98% identical to SEQ ID NO: 14.

20. The isolated nucleic acid molecule of claim 1, wherein the nucleic acid sequence comprises a sequence that is at least 90% identical to SEQ ID NO: 12.

21. The isolated nucleic acid molecule of claim 1, wherein the nucleic acid sequence comprises a sequence that is at least 90% identical to SEQ ID NO: 13.

22. The isolated nucleic acid molecule of claim 1, wherein the nucleic acid sequence comprises a sequence that is at least 95% identical to SEQ ID NO: 12.

23. The isolated nucleic acid molecule of claim 1, wherein the nucleic acid sequence comprises a sequence that is at least 95% identical to SEQ ID NO: 13.

* * * * *

SEQUENCE LISTING

<160> NUMBER OF SEQ ID NOS: 34

<210> SEQ ID NO 1
<211> LENGTH: 1068
<212> TYPE: DNA
<213> ORGANISM: Mortierella ramanniana

<400> SEQUENCE: 1

```
atggccagca aggatcaaca tttacagcag aaggtcaagc atacgctaga agctatccca    60
tcccctcgct atgctccatt gcgagtgcca ttaagacgga gattacaaac attggcagtt   120
ttattatggt gttccatgat gtcaatatgc atgttcatat tcttcttttt atgctccatt   180
cctgttctcc tttggttccc cattatcctt tatttgacct ggatcttggt gtgggataag   240
gcgccagaga acggtggaag acctattcgc tggctgcgga atgctgcttg gtggaagctg   300
tttgcagggt attttccgc acatgtcatc aaggaagccg attagatcc atccaagaac    360 tacatctttg ttatcaccc ccatggaatc atatccatgg gctcgttctg tacttttagt    420
accaatgcta ctggctttga tgacttgttc ccaggcatcc ggccatcgct tttgacatta    480
acatctaatt ttaatatccc actttatcgt gattatttga tggcgtgcgg actttgctcc    540
gtctccaaaa catcctgtca aaatatttta accaaaggtg gtccgggccg ttccattgcc    600
attgtcgtgg gaggtgcttc cgagtctctc aatgctagac ccggtgtcat ggaccttgtg    660
ttgaagagac gctttggttt tatcaagatt gctgttcaaa ccggtgcaag tctagtgccc    720
actatcagtt ttggtgaaaa tgagctgtac gaacagattg aaagcaatga aaactcaaag    780
ttgcatagat ggcaaaagaa gattcaacat gcccttggtt ttactatgcc gctcttcat    840 ggacgcggtg tattcaatta tgactttggt ttgctccccc atcgccatcc tatctacacg    900
attgttggaa agcccatccc cgtccctagc atcaagtatg acagacaaa ggatgagatt    960 ataagagaac tacatgactc gtacatgcat gccgtgcagg atctctatga tcgttacaag   1020
gatatctatg caaaggatcg ggtaaaagaa ctagaattcg tcgaatag                1068

<210> SEQ ID NO 2
<211> LENGTH: 355
<212> TYPE: PRT
<213> ORGANISM: Mortierella ramanniana

<400> SEQUENCE: 2

Met Ala Ser Lys Asp Gln His Leu Gln Gln Lys Val Lys His Thr Leu
1               5                   10                  15

Glu Ala Ile Pro Ser Pro Arg Tyr Ala Pro Leu Arg Val Pro Leu Arg
                20                  25                  30

Arg Arg Leu Gln Thr Leu Ala Val Leu Leu Trp Cys Ser Met Met Ser
        35                  40                  45

Ile Cys Met Phe Ile Phe Phe Leu Cys Ser Ile Pro Val Leu Leu
    50                  55                  60

Trp Phe Pro Ile Ile Leu Tyr Leu Thr Trp Ile Leu Val Trp Asp Lys
65                  70                  75                  80

Ala Pro Glu Asn Gly Gly Arg Pro Ile Arg Trp Leu Arg Asn Ala Ala
                85                  90                  95

Trp Trp Lys Leu Phe Ala Gly Tyr Phe Pro Ala His Val Ile Lys Glu
            100                 105                 110

Ala Asp Leu Asp Pro Ser Lys Asn Tyr Ile Phe Gly Tyr His Pro His
        115                 120                 125

Gly Ile Ile Ser Met Gly Ser Phe Cys Thr Phe Ser Thr Asn Ala Thr
    130                 135                 140

Gly Phe Asp Asp Leu Phe Pro Gly Ile Arg Pro Ser Leu Leu Thr Leu
145                 150                 155                 160

Thr Ser Asn Phe Asn Ile Pro Leu Tyr Arg Asp Tyr Leu Met Ala Cys
                165                 170                 175

Gly Leu Cys Ser Val Ser Lys Thr Ser Cys Gln Asn Ile Leu Thr Lys
            180                 185                 190
```

```
Gly Gly Pro Gly Arg Ser Ile Ala Ile Val Val Gly Gly Ala Ser Glu
            195                 200                 205
Ser Leu Asn Ala Arg Pro Gly Val Met Asp Leu Val Leu Lys Arg Arg
        210                 215                 220
Phe Gly Phe Ile Lys Ile Ala Val Gln Thr Gly Ala Ser Leu Val Pro
225                 230                 235                 240
Thr Ile Ser Phe Gly Glu Asn Glu Leu Tyr Glu Gln Ile Glu Ser Asn
                245                 250                 255
Glu Asn Ser Lys Leu His Arg Trp Gln Lys Lys Ile Gln His Ala Leu
            260                 265                 270
Gly Phe Thr Met Pro Leu Phe His Gly Arg Gly Val Phe Asn Tyr Asp
        275                 280                 285
Phe Gly Leu Leu Pro His Arg His Pro Ile Tyr Thr Ile Val Gly Lys
290                 295                 300
Pro Ile Pro Val Pro Ser Ile Lys Tyr Gly Gln Thr Lys Asp Glu Ile
305                 310                 315                 320
Ile Arg Glu Leu His Asp Ser Tyr Met His Ala Val Gln Asp Leu Tyr
                325                 330                 335
Asp Arg Tyr Lys Asp Ile Tyr Ala Lys Asp Arg Val Lys Glu Leu Glu
            340                 345                 350
Phe Val Glu
        355

<210> SEQ ID NO 3
<211> LENGTH: 1050
<212> TYPE: DNA
<213> ORGANISM: Mortierella ramanniana

<400> SEQUENCE: 3
atggaacaag tccaagtcac tgcattgctc gaccacattc ccaaagtcca ttgggcaccg      60
ctccgtggga tcccttgaa gcgtcgctta caaacgtcgg ctatcgtcac atggctggct     120
ttgcttccta tctgtctcat tatataccng tacctattca ccattccctt attatggccc     180
atcctcatta tgtatacgat atggctgttt ttcgacaaag cccctgaaaa cggaggcaga     240
cgaatttcgc tggtgaggaa attgccgctg tggaagcatt ttgccaatta tttcccagtc     300
cctttgatca aggaaggaga cctcgacccc aagggaaact acatcatgtc atatcatccg     360
catggaataa tatccatggc ggcttttgcc aattttgcga ctgaggcgac tgggttttcc     420
gagcaatatc cgggtattgt tccttcatta ctgacgctag catccaattt tcggttgcca     480
ttgtaccgag atttcatgat gtcactaggc atgtgctcgg tatcgcgaca ctcctgtgaa     540
gctatccttc gttcggggcc cggtcgatcc attgtgattg ttacaggcgg agcttcagaa     600
tcccttagcg cacgaccagg caccaacgac ctcaccctca gaaacgatt gggtttcatc     660
cgactagcca ttcgaaatgg tgccagttta gtgcctatct tttcgtttgg agagaacgac     720
atctacgagc aatatgataa caaaaagggc agtttgatat ggcggtacca aaaatggttc     780
caaaaaatta caggattcac ggttcctttg gctcatgccc gtggcatttt caactacaat     840
gctgggttta taccattccg acatccgata gtgacagttg ttggcaaacc tattgctgtc     900
cccctcttgg ctgaaggcga aaccgaacct agcgaggagc aaatgcatca agttcaagca     960
cagtacattg aaagtttgca ggctatttat gataaataca agatattta tgctaaggat    1020
agaataaaag atatgaccat gattgcataa                                     1050
```

<210> SEQ ID NO 4
<211> LENGTH: 349
<212> TYPE: PRT
<213> ORGANISM: Mortierella ramanniana

<400> SEQUENCE: 4

```
Met Glu Gln Val Gln Val Thr Ala Leu Leu Asp His Ile Pro Lys Val
1               5                   10                  15

His Trp Ala Pro Leu Arg Gly Ile Pro Leu Lys Arg Arg Leu Gln Thr
            20                  25                  30

Ser Ala Ile Val Thr Trp Leu Ala Leu Leu Pro Ile Cys Leu Ile Ile
        35                  40                  45

Tyr Leu Tyr Leu Phe Thr Ile Pro Leu Leu Trp Pro Ile Leu Ile Met
    50                  55                  60

Tyr Thr Ile Trp Leu Phe Phe Asp Lys Ala Pro Glu Asn Gly Gly Arg
65                  70                  75                  80

Arg Ile Ser Leu Val Arg Lys Leu Pro Leu Trp Lys His Phe Ala Asn
                85                  90                  95

Tyr Phe Pro Val Pro Leu Ile Lys Glu Gly Asp Leu Asp Pro Lys Gly
            100                 105                 110

Asn Tyr Ile Met Ser Tyr His Pro His Gly Ile Ile Ser Met Ala Ala
        115                 120                 125

Phe Ala Asn Phe Ala Thr Glu Ala Thr Gly Phe Ser Glu Gln Tyr Pro
    130                 135                 140

Gly Ile Val Pro Ser Leu Leu Thr Leu Ala Ser Asn Phe Arg Leu Pro
145                 150                 155                 160

Leu Tyr Arg Asp Phe Met Met Ser Leu Gly Met Cys Ser Val Ser Arg
                165                 170                 175

His Ser Cys Glu Ala Ile Leu Arg Ser Gly Pro Gly Arg Ser Ile Val
            180                 185                 190

Ile Val Thr Gly Gly Ala Ser Glu Ser Leu Ser Ala Arg Pro Gly Thr
        195                 200                 205

Asn Asp Leu Thr Leu Lys Lys Arg Leu Gly Phe Ile Arg Leu Ala Ile
    210                 215                 220

Arg Asn Gly Ala Ser Leu Val Pro Ile Phe Ser Phe Gly Glu Asn Asp
225                 230                 235                 240

Ile Tyr Glu Gln Tyr Asp Asn Lys Lys Gly Ser Leu Ile Trp Arg Tyr
                245                 250                 255

Gln Lys Trp Phe Gln Lys Ile Thr Gly Phe Thr Val Pro Leu Ala His
            260                 265                 270

Ala Arg Gly Ile Phe Asn Tyr Asn Ala Gly Phe Ile Pro Phe Arg His
        275                 280                 285

Pro Ile Val Thr Val Val Gly Lys Pro Ile Ala Val Pro Leu Leu Ala
    290                 295                 300

Glu Gly Glu Thr Glu Pro Ser Glu Glu Gln Met His Gln Val Gln Ala
305                 310                 315                 320

Gln Tyr Ile Glu Ser Leu Gln Ala Ile Tyr Asp Lys Tyr Lys Asp Ile
                325                 330                 335

Tyr Ala Lys Asp Arg Ile Lys Asp Met Thr Met Ile Ala
            340                 345
```

<210> SEQ ID NO 5
<211> LENGTH: 1257
<212> TYPE: DNA
<213> ORGANISM: Saccharomyces cerevisiae

```
<400> SEQUENCE: 5
atgtcaggaa cattcaatga tataagaaga aggaagaagg aagaaggaag ccctacagcc      60
ggtattaccg aaaggcatga aataagtct ttgtcaagca tcgataaaag agaacagact     120
ctcaaaccac aactagagtc atgctgtcca ttggcgaccc cttttgaaag aaggttacaa    180
actctggctg tagcatggca cacttcttca tttgtactct tctccatatt tacgttattt    240
gcaatctcga caccagcact gtgggttctt gctattccat atatgattta ttttttttc    300 gataggtctc ctgcaactgg cgaagtggta atcgatact ctcttcgatt cgttcattg     360 cccatttgga agtggtattg tgattatttc cctataagtt tgattaaaac tgtcaattta    420
aaaccaactt ttacgctttc aaaaaataag agagttaacg aaaaaaatta caagattaga    480
ttgtggccaa ctaagtattc cattaatctc aaaagcaact ctactattga ctatcgcaac    540
caggaatgta cagggccaac gtacttattt ggttaccatc cacacggcat aggagcactt    600
ggtgcgtttg agcgtttgc aacagaaggt tgtaactatt ccaagatttt cccaggtatt     660
cctatttctc tgatgacact ggtcacacaa tttcatatcc cattgtatag agactactta    720
ttggcgttag gtatttcttc agtatctcgg aaaaacgctt taaggactct aagcaaaaat    780
cagtcgatct gcattgttgt tggtggcgct agggaatctt tattaagttc aacaaatggt    840
acacaactga ttttaaacaa agaaagggt tttattaaac tggccattca acggggaat     900 attaacctag tgcctgtgtt tgcatttgga gaggtggact gttataatgt tctgagcaca    960
aaaaaagatt cagtcctggg taaatgcaa ctatggttca agaaaacttt ggttttacc    1020 attcccattt tctacgcaag aggattattc aattacgatt tcggtttgtt gccatttaga   1080
gcgcctatca atgttgttgt tggaaggcct atatacgttg aaaagaaaat aacaaatccg   1140
ccagatgatg ttgttaatca tttccatgat ttgtatattg cggagttgaa aagactatat   1200
tacgaaaata gagaaaaata tggggtaccg gatgcagaat tgaagatagt tgggtaa      1257

<210> SEQ ID NO 6
<211> LENGTH: 418
<212> TYPE: PRT
<213> ORGANISM: Saccharomyces cerevisiae

<400> SEQUENCE: 6

Met Ser Gly Thr Phe Asn Asp Ile Arg Arg Arg Lys Lys Glu Glu Gly
1               5                   10                  15

Ser Pro Thr Ala Gly Ile Thr Glu Arg His Glu Asn Lys Ser Leu Ser
            20                  25                  30

Ser Ile Asp Lys Arg Glu Gln Thr Leu Lys Pro Gln Leu Glu Ser Cys
        35                  40                  45

Cys Pro Leu Ala Thr Pro Phe Glu Arg Arg Leu Gln Thr Leu Ala Val
    50                  55                  60

Ala Trp His Thr Ser Ser Phe Val Leu Phe Ser Ile Phe Thr Leu Phe
65                  70                  75                  80

Ala Ile Ser Thr Pro Ala Leu Trp Val Leu Ala Ile Pro Tyr Met Ile
                85                  90                  95

Tyr Phe Phe Phe Asp Arg Ser Pro Ala Thr Gly Glu Val Val Asn Arg
            100                 105                 110

Tyr Ser Leu Arg Phe Arg Ser Leu Pro Ile Trp Lys Trp Tyr Cys Asp
        115                 120                 125

Tyr Phe Pro Ile Ser Leu Ile Lys Thr Val Asn Leu Lys Pro Thr Phe
    130                 135                 140
```

```
Thr Leu Ser Lys Asn Lys Arg Val Asn Glu Lys Asn Tyr Lys Ile Arg
145                 150                 155                 160

Leu Trp Pro Thr Lys Tyr Ser Ile Asn Leu Lys Ser Asn Ser Thr Ile
                165                 170                 175

Asp Tyr Arg Asn Gln Glu Cys Thr Gly Pro Thr Tyr Leu Phe Gly Tyr
            180                 185                 190

His Pro His Gly Ile Gly Ala Leu Gly Ala Phe Gly Ala Phe Ala Thr
        195                 200                 205

Glu Gly Cys Asn Tyr Ser Lys Ile Phe Pro Gly Ile Pro Ile Ser Leu
    210                 215                 220

Met Thr Leu Val Thr Gln Phe His Ile Pro Leu Tyr Arg Asp Tyr Leu
225                 230                 235                 240

Leu Ala Leu Gly Ile Ser Ser Val Ser Arg Lys Asn Ala Leu Arg Thr
                245                 250                 255

Leu Ser Lys Asn Gln Ser Ile Cys Ile Val Val Gly Gly Ala Arg Glu
            260                 265                 270

Ser Leu Leu Ser Ser Thr Asn Gly Thr Gln Leu Ile Leu Asn Lys Arg
        275                 280                 285

Lys Gly Phe Ile Lys Leu Ala Ile Gln Thr Gly Asn Ile Asn Leu Val
    290                 295                 300

Pro Val Phe Ala Phe Gly Glu Val Asp Cys Tyr Asn Val Leu Ser Thr
305                 310                 315                 320

Lys Lys Asp Ser Val Leu Gly Lys Met Gln Leu Trp Phe Lys Glu Asn
                325                 330                 335

Phe Gly Phe Thr Ile Pro Ile Phe Tyr Ala Arg Gly Leu Phe Asn Tyr
            340                 345                 350

Asp Phe Gly Leu Leu Pro Phe Arg Ala Pro Ile Asn Val Val Val Gly
        355                 360                 365

Arg Pro Ile Tyr Val Glu Lys Lys Ile Thr Asn Pro Pro Asp Asp Val
    370                 375                 380

Val Asn His Phe His Asp Leu Tyr Ile Ala Glu Leu Lys Arg Leu Tyr
385                 390                 395                 400

Tyr Glu Asn Arg Glu Lys Tyr Gly Val Pro Asp Ala Glu Leu Lys Ile
                405                 410                 415

Val Gly

<210> SEQ ID NO 7
<211> LENGTH: 43
<212> TYPE: DNA
<213> ORGANISM: Artificial
<220> FEATURE:
<223> OTHER INFORMATION: Primer

<400> SEQUENCE: 7
ggatcccggt ccgaagcgcg catggagcgg gatagagcca acg                    43

<210> SEQ ID NO 8
<211> LENGTH: 42
<212> TYPE: DNA
<213> ORGANISM: Artificial
<220> FEATURE:
<223> OTHER INFORMATION: Primer

<400> SEQUENCE: 8
aagcttggta ccctatttca gtatctgcat ttcctcaatc cg                     42

<210> SEQ ID NO 9
```

```
<211> LENGTH: 34
<212> TYPE: DNA
<213> ORGANISM: Artificial
<220> FEATURE:
<223> OTHER INFORMATION: Primer

<400> SEQUENCE: 9
aaaagcggcc gcatggagcg ggatagagcc aacg                         34

<210> SEQ ID NO 10
<211> LENGTH: 33
<212> TYPE: DNA
<213> ORGANISM: Artificial
<220> FEATURE:
<223> OTHER INFORMATION: Primer

<400> SEQUENCE: 10
aaaacctgca ggctatttca gtatctgcat ttc                          33

<210> SEQ ID NO 11
<211> LENGTH: 1050
<212> TYPE: DNA
<213> ORGANISM: Mortierella ramanniana

<400> SEQUENCE: 11
atggagcaag ttcaggttac agcactcctc gatcacatcc ctaaagtgca ttgggcccct    60
cttaggggta ttcctttgaa acgcagattg caaacttcag ccatcgttac ctggctcgca   120
ctcctcccta tatgcctcat aatataccct tacctcttca ccatccctct tctctggcca   180
attcttatca tgtacaccat ctggctattt ttcgacaaag ctcccgaaaa cggtggtcgt   240
agaatctcct tggtcagaaa acttccccta tggaaacact tcgcaaacta cttccctgtc   300
acactcatta agagggggga ccttgaccca aaaggaaact acataatgag ctaccatcca   360
cacggtatca tctctatggc agccttcgcc aacttcgcta ccgaggcaac cggtttctcc   420
gaacaatacc ctggtatcgt gccaagcctt ctaaccctcg cctctaactt cagacttcca   480
ttgtatagag acttcatgat gtccctcggt atgtgctctg ttagtcgtca ctcctgtgaa   540
gcaatactta gatccggacc aggaaggagt atcgttatag ttaccggtgg agcctctgaa   600
tccctcagtg ctagacccgg cacgaatgat ttgacccta agaagagact cggttttatt   660
cgtctcgcaa taagaaacgg cgctagtctt gtgcctattt tcagtttcgg tgaaaatgac   720
atttacgagc aatacgataa taaaaagggc tcccttatct ggcgttacca gaagtggttc   780
cagaagatta ccggattcac tgtcccactt gctcacgccc gcgtatatt caactataat   840
gccggtttca tccctttag gcaccctatc gtcacagttg tcggtaaacc aatcgcagtt   900
ccattgcttg ctgaaggaga gacagagcca tccgaggagc agatgcacca agtccaggca   960
caatatattg agagtcttca ggctatatac gacaagtaca agatattta tgctaaagat  1020
cgcattaaag acatgactat gatcgcctaa                                   1050

<210> SEQ ID NO 12
<211> LENGTH: 1059
<212> TYPE: DNA
<213> ORGANISM: Neurospora crassa

<400> SEQUENCE: 12
atggaaagag atagagctaa tgcctaccaa gcagccggaa taagattcgc ccctttcaac    60
ataccacttc aaagacgtct ccaaacactt gcagtcctac ttcacagcct cattatagct   120
accaccgttt cattcttctt ttttctctgc gcgataccac tactatggcc tcttgttatc   180
```

-continued

```
ccctatctcc ttcatatgct cctctccaaa gccgcaagcg acgggaaact caggttcaga      240
tcagaacgct ttagacactc cagaatatgg cacttttcg cagattactt cccagctaaa       300
ctacacaaaa ctcacgactt gccagcagat agaaaataca ttttcggtta tcatccccac     360
ggtataatct cacatggtgc ttacgctgcc ttcgcaacag aagctctcgg atttagtgaa     420
aaattcccag gtataacaaa ctcacttctc actcttgaca gcaatttcag aatcccaatt    480
taccgcgact acattctctc catgggcctc agatcagtta gcaaagaatc tatcacgaac    540
attctctctc gcggtggaac tgatggacac ggcgccggta gggctgttac tattgtgatc     600
ggcggtgcca gggaatcact cgaagctcaa cccggaactc tcagacttgt gctaggtgaa    660
cgcaaaggct tcgttaaagt tgcaatgaga accggagcag atattgtgcc agttcttgct     720
ttcggtgaaa acgacccttta cgaccaagtt tctccaaaat cacacccttaa ccttcataga  780 ctccaaatgt tcgttctcag aaccctcaaa ttcacacttc cctttctcca cggacgcgga   840
atctttaact acgacgtcgg actcatgcct tatagaagac cactcaacat cgttgttgga   900
aagccaatta gggttacaaa acgtgccgaa tcagacctag aaaccagcga aattgaccaa   960
cttcacggcc tttatgttaa ggaactagaa aaaatgtggg aacgctacaa agatggattc  1020 gccccctgaaa gaattgaaga aatgcagatc cttaaataa                          1059
```

<210> SEQ ID NO 13
<211> LENGTH: 1059
<212> TYPE: DNA
<213> ORGANISM: Neurospora crassa

<400> SEQUENCE: 13

```
atggagcggg atagagccaa cgcataccag gctgccggca tcagatttgc gccatttaac      60 ataccttac agcgaagact ccagaccctg gcggttctgc tacactcgct gattattgcc     120
actaccgtat ccttctttt cttcctgtgc gccatccctt tactctggcc attggttatc     180
ccatatcttc ttcatatgct gcttagcaaa gcagcatccg atggaaagtt gcgcttccgc    240
tcagaaagat tccggcactc ccgaatctgg cacttcttg cagactactt cccggctaag      300
ctgcacaaga cgcacgatct tcccgccgat aggaagtaca tctttggtta tcaccccac     360 ggcatcatct cacatggcgc ttacgccgct tttgccaccg aagccctcgg tttctctgag    420 aaattcccccg gaattaccaa cagcctgctt accctggaca gtaacttccg cattccgatt    480
taccgcgact atatccttag catgggcctc cgctccgttt cgaaggagtc aatcaccaat    540
atcctcagcc gcggcggtac tgacggtcac ggcgcgggcc gtgctgttac cattgttatt    600
ggtggtgctc gagaatcact ggaggctcaa cctggtacac tccgtctcgt gctcggcgag    660
cgcaagggct tcgtcaaggt ggccatgcgc actggcgctg acatcgtccc cgtgctcgca    720
tttggcgaga acgatctcta cgatcaggtc agtcccaaga gccatccgta cttgcatagg    780
ctccagatgt ttgtgctccg aaccctcaag ttcactctgc cgttttttgca tggaagaggc    840 atttttcaact acgatgtggg cctgatgcca taccgccggc cgttgaacat tgttgtcggc    900
aagccgatcc gggttacaaa agggccgag agcgacctgg agacaagcga gattgaccag    960
ctacacggcc tttatgtaaa ggagctggaa aagatgtggg agcgctacaa ggacgggttt    1020
gccccagaac ggattgagga aatgcagata ctgaaatag                            1059
```

<210> SEQ ID NO 14
<211> LENGTH: 352
<212> TYPE: PRT

<213> ORGANISM: Neurospora crassa

<400> SEQUENCE: 14

| | | | | | | | | | | | | | | | |
|---|---|---|---|---|---|---|---|---|---|---|---|---|---|---|---|
| Met | Glu | Arg | Asp | Arg | Ala | Asn | Ala | Tyr | Gln | Ala | Ala | Gly | Ile | Arg | Phe |
| 1 | | | | 5 | | | | | 10 | | | | | 15 | |
| Ala | Pro | Phe | Asn | Ile | Pro | Leu | Gln | Arg | Arg | Leu | Gln | Thr | Leu | Ala | Val |
| | | | 20 | | | | | 25 | | | | | 30 | | |
| Leu | Leu | His | Ser | Leu | Ile | Ile | Ala | Thr | Thr | Val | Ser | Phe | Phe | Phe | Phe |
| | | | 35 | | | | 40 | | | | | 45 | | | |
| Leu | Cys | Ala | Ile | Pro | Leu | Leu | Trp | Pro | Leu | Val | Ile | Pro | Tyr | Leu | Leu |
| | 50 | | | | | 55 | | | | | 60 | | | | |
| His | Met | Leu | Leu | Ser | Lys | Ala | Ala | Ser | Asp | Gly | Lys | Leu | Arg | Phe | Arg |
| 65 | | | | | 70 | | | | | 75 | | | | | 80 |
| Ser | Glu | Arg | Phe | Arg | His | Ser | Arg | Ile | Trp | His | Phe | Phe | Ala | Asp | Tyr |
| | | | | 85 | | | | | 90 | | | | | 95 | |
| Phe | Pro | Ala | Lys | Leu | His | Lys | Thr | His | Asp | Leu | Pro | Ala | Asp | Arg | Lys |
| | | | 100 | | | | | 105 | | | | | 110 | | |
| Tyr | Ile | Phe | Gly | Tyr | His | Pro | His | Gly | Ile | Ile | Ser | His | Gly | Ala | Tyr |
| | | | | 115 | | | | | 120 | | | | | 125 | |
| Ala | Ala | Phe | Ala | Thr | Glu | Ala | Leu | Gly | Phe | Ser | Glu | Lys | Phe | Pro | Gly |
| | 130 | | | | | 135 | | | | | 140 | | | | |
| Ile | Thr | Asn | Ser | Leu | Leu | Thr | Leu | Asp | Ser | Asn | Phe | Arg | Ile | Pro | Ile |
| 145 | | | | | 150 | | | | | 155 | | | | | 160 |
| Tyr | Arg | Asp | Tyr | Ile | Leu | Ser | Met | Gly | Leu | Arg | Ser | Val | Ser | Lys | Glu |
| | | | | 165 | | | | | 170 | | | | | 175 | |
| Ser | Ile | Thr | Asn | Ile | Leu | Ser | Arg | Gly | Gly | Thr | Asp | Gly | His | Gly | Ala |
| | | | 180 | | | | | 185 | | | | | 190 | | |
| Gly | Arg | Ala | Val | Thr | Ile | Val | Ile | Gly | Gly | Ala | Arg | Glu | Ser | Leu | Glu |
| | | 195 | | | | | 200 | | | | | 205 | | | |
| Ala | Gln | Pro | Gly | Thr | Leu | Arg | Leu | Val | Leu | Gly | Glu | Arg | Lys | Gly | Phe |
| | 210 | | | | | 215 | | | | | 220 | | | | |
| Val | Lys | Val | Ala | Met | Arg | Thr | Gly | Ala | Asp | Ile | Val | Pro | Val | Leu | Ala |
| 225 | | | | | 230 | | | | | 235 | | | | | 240 |
| Phe | Gly | Glu | Asn | Asp | Leu | Tyr | Asp | Gln | Val | Ser | Pro | Lys | Ser | His | Pro |
| | | | | 245 | | | | | 250 | | | | | 255 | |
| Tyr | Leu | His | Arg | Leu | Gln | Met | Phe | Val | Leu | Arg | Thr | Leu | Lys | Phe | Thr |
| | | | 260 | | | | | 265 | | | | | 270 | | |
| Leu | Pro | Phe | Leu | His | Gly | Arg | Gly | Ile | Phe | Asn | Tyr | Asp | Val | Gly | Leu |
| | | 275 | | | | | 280 | | | | | 285 | | | |
| Met | Pro | Tyr | Arg | Arg | Pro | Leu | Asn | Ile | Val | Val | Gly | Lys | Pro | Ile | Arg |
| | 290 | | | | | 295 | | | | | 300 | | | | |
| Val | Thr | Lys | Arg | Ala | Glu | Ser | Asp | Leu | Glu | Thr | Ser | Glu | Ile | Asp | Gln |
| 305 | | | | | 310 | | | | | 315 | | | | | 320 |
| Leu | His | Gly | Leu | Tyr | Val | Lys | Glu | Leu | Glu | Lys | Met | Trp | Glu | Arg | Tyr |
| | | | | 325 | | | | | 330 | | | | | 335 | |
| Lys | Asp | Gly | Phe | Ala | Pro | Glu | Arg | Ile | Glu | Glu | Met | Gln | Ile | Leu | Lys |
| | | | 340 | | | | | 345 | | | | | 350 | | |

<210> SEQ ID NO 15
<211> LENGTH: 1068
<212> TYPE: DNA
<213> ORGANISM: Mortierella ramannaina

<400> SEQUENCE: 15
atggctagca aggaccagca cctccaacag aaggtgaagc acacccttga ggccatccca    60

```
tcccctaggt atgctccact cagggtccca cttaggagaa ggctccaaac ccttgctgtt      120
ctcctctggt gctccatgat gagcatctgc atgttcatct tcttcttcct ctgcagcatc      180
cctgtgctcc tttggttccc aattatcctc tacttgacct ggattttggt gtgggataag      240
gcccctgaga acggaggcag acctatcagg tggctcagga acgcagcttg gtggaagctc      300
tttgctggat acttcccagc tcatgttatc aaggaggctg accttgaccc atccaagaac      360
tacatctttg gttaccaccc acatggtatc atcagcatgg gtagcttctg caccttctcc      420
accaacgcta ctggtttcga tgacctcttc ccaggaatca ggccttcctt gctcacccct      480
accagcaact tcaacatccc actctacagg gattacctca tggcctgtgg actctgctca      540
gtgtctaaga cctcctgcca gaacatcctc accaagggtg tccaggaag gtccattgct       600 attgtggtgg gaggtgcctc tgagtccttg aacgccagac caggagtgat ggaccttgtg      660
ttgaagagga ggtttggttt catcaagatt gctgtgcaga ctggtgctag ccttgtccct      720
accatctcct ttggtgagaa tgagctttat gagcagattg agagcaatga gaactctaag      780
cttcacaggt ggcagaagaa gatccagcat gctcttggtt tcaccatgcc actcttccat      840 ggaagggggtg tgttcaacta cgactttggt ctcctcccac acaggcaccc aatttacacc      900
attgtgggta agccaatccc agtcccatct atcaagtacg gtcagaccaa ggatgagatc      960
atcagggagc tccatgactc ttacatgcac gctgtgcagg acctctatga caggtacaag     1020
gacatctacg ccaaggacag ggtcaaggag cttgagtttg tcgagtga                  1068

<210> SEQ ID NO 16
<211> LENGTH: 1257
<212> TYPE: DNA
<213> ORGANISM: Saccharomyces cerevisiae

<400> SEQUENCE: 16
atgtctggaa cattcaacga tattagaaga aggaagaagg aggagggaag ccctacagcc       60
ggtattaccg agaggcatga gaacaagtct ttgtctagca tcgataagag agagcagact      120
ctcaaaccac aactcgagtc ttgctgccca ttggctaccc cttttgagag aaggcttcaa      180
actcttgctg tggcatggca cacttcttct tttgtgctct tctccatttt tactctttt      240 gcaatctcta caccagcact ttgggttctt gctattccat acatgattta ctttttttc       300 gataggtctc ctgcaactgg cgaggtggtg aacagatact ctcttagatt tagatctttg      360
cccatttgga gtggtactg cgattacttc cctatttctt tgattaagac tgtcaacctt      420
aagccaactt ttactctttc taagaacaag agagttaacg agaagaacta caagattaga      480
ttgtggccaa ctaagtactc cattaacctc aagagcaact ctactattga ctaccgcaac      540
caggagtgca cagggccaac ttaccttttt ggttaccatc cacacggcat ggagcactt       600 ggtgcttttg gagcttttgc aacagagggt tgcaactact ccaagatttt cccaggtatt      660
cctatttctc ttatgacact tgtcacacaa tttcatatcc cattgtacag agactacctt      720
ttggctcttg gtatttcttc tgtgtctaga aagaacgctc ttaggactct cagcaagaac      780
cagtctatct gcattgttgt tggtggcgct agggagtctc ttctttcttc tacaaacggt      840
acacaactta ttcttaacaa gagaaagggt tttattaaac ttgccattca aactgggaac      900
attaacctcg tgcctgtgtt tgcatttgga gaggtggact gctacaacgt tcttagcaca      960
aagaaggatt ctgtccttgg taagatgcaa ctctggttca aggagaactt tggtttttacc     1020 attcccattt tctacgcaag aggactttc aactacgatt tcggtttgtt gccatttaga     1080
```

-continued

```
gctcctatca acgttgttgt tggaaggcct atttacgttg agaagaagat tacaaacccg    1140
ccagatgatg ttgttaacca tttccatgat ttgtacattg ctgagttgaa agagactctac   1200 tacgagaaca gagagaagta cggggtgccg gatgcagagt tgaagatagt tgggtaa       1257
```

<210> SEQ ID NO 17
<211> LENGTH: 1002
<212> TYPE: DNA
<213> ORGANISM: Hordeum vulgare

<400> SEQUENCE: 17

```
atgggcgcga atggcgcgct ggaggaggag aggccgcggg ccgacggcgg cgacgaggag      60
ggcggggcga cggtgttccg ggcaccaac tactcgctgc cgcggacgat cgccgcgctg     120
gcgctgtggc tcgggggaat ccacttcaac gtcctcctca tcctcgcctc cctcttcctc    180
ttcccgctcc gcctcgccgc gctggtggtg gcgttgcagc tcatgttcat gttcatcccc    240
ctcaacgacg aggacaaact cggccgaaaa atcggcaggt tcatatgcaa gtacgccatg    300
gggtacttcc cgattagctt gcacgtggag gactacgagg ccttcgactc cagcagggct    360
tacgtgtttg gctatgaacc gcattccgtg ctgcccatcg gcgtggcggc tctggccaac    420
catgtcgggt ttatgcctct tcctaagctc aaagtcctcg cgagcagcgc ggtgttccac    480
accccattcc tgaggcagat atggacgtgg atagggctga tcgcggcaac gaggaagaat    540
ttctactcgt accttgcggc gggttacagt tgcgtcgtgg tgcccggagg tatacaggag    600
attcttcata tggatcatga ttccgaggtt gctttcctta aatcaagaaa agggtttgtc    660
aagatagcta tgcagtctgg ctgcccttta gtccctgtct tctgcttcgg acagagcaaa    720
gcttacaagt ggtggaggcc aggaggcaaa ttgtttgtga acattgctag ggcacttaaa    780
tttaccccta ttatcttctg gggaagatac gggacgccga tcgctttctc gtcacctatg    840
catgtggttg ttggaagacc cattgagctg aagaaaaatc tctgcctac cattgatgag    900 ataaacgaag tgcacgggca attcatcggc gccttgcaag aactgtttga aagtacaag     960 acgaaagccg gatatccgg cctccatctg cgagtcctat aa                       1002
```

<210> SEQ ID NO 18
<211> LENGTH: 333
<212> TYPE: PRT
<213> ORGANISM: Hordeum vulgare

<400> SEQUENCE: 18

```
Met Gly Ala Asn Gly Ala Leu Glu Glu Glu Arg Pro Arg Ala Asp Gly
1               5                   10                  15

Gly Asp Glu Glu Gly Gly Ala Thr Val Phe Arg Gly Thr Asn Tyr Ser
            20                  25                  30

Leu Pro Arg Thr Ile Ala Ala Leu Ala Leu Trp Leu Gly Gly Ile His
        35                  40                  45

Phe Asn Val Leu Leu Ile Leu Ala Ser Leu Phe Leu Phe Pro Leu Arg
    50                  55                  60

Leu Ala Ala Leu Val Val Ala Leu Gln Leu Met Phe Met Phe Ile Pro
65                  70                  75                  80

Leu Asn Asp Glu Asp Lys Leu Gly Arg Lys Ile Gly Arg Phe Ile Cys
                85                  90                  95

Lys Tyr Ala Met Gly Tyr Phe Pro Ile Ser Leu His Val Glu Asp Tyr
            100                 105                 110

Glu Ala Phe Asp Ser Ser Arg Ala Tyr Val Phe Gly Tyr Glu Pro His
        115                 120                 125
```

Ser Val Leu Pro Ile Gly Val Ala Ala Leu Ala Asn His Val Gly Phe
    130                 135                 140

Met Pro Leu Pro Lys Leu Lys Val Leu Ala Ser Ser Ala Val Phe His
145                 150                 155                 160

Thr Pro Phe Leu Arg Gln Ile Trp Thr Trp Ile Gly Leu Ile Ala Ala
                165                 170                 175

Thr Arg Lys Asn Phe Tyr Ser Tyr Leu Ala Ala Gly Tyr Ser Cys Val
            180                 185                 190

Val Val Pro Gly Gly Ile Gln Glu Ile Leu His Met Asp His Asp Ser
        195                 200                 205

Glu Val Ala Phe Leu Lys Ser Arg Lys Gly Phe Val Lys Ile Ala Met
    210                 215                 220

Gln Ser Gly Cys Pro Leu Val Pro Val Phe Cys Phe Gly Gln Ser Lys
225                 230                 235                 240

Ala Tyr Lys Trp Trp Arg Pro Gly Gly Lys Leu Phe Val Asn Ile Ala
                245                 250                 255

Arg Ala Leu Lys Phe Thr Pro Ile Ile Phe Trp Gly Arg Tyr Gly Thr
            260                 265                 270

Pro Ile Ala Phe Ser Ser Pro Met His Val Val Gly Arg Pro Ile
        275                 280                 285

Glu Leu Lys Lys Asn Pro Leu Pro Thr Ile Asp Glu Ile Asn Glu Val
    290                 295                 300

His Gly Gln Phe Ile Gly Ala Leu Gln Glu Leu Phe Glu Lys Tyr Lys
305                 310                 315                 320

Thr Lys Ala Gly Tyr Pro Gly Leu His Leu Arg Val Leu
                325                 330

<210> SEQ ID NO 19
<211> LENGTH: 1002
<212> TYPE: DNA
<213> ORGANISM: Zea mays

<400> SEQUENCE: 19
atgggggcgg gaaccaataa tggcctgagc aacggcgccg ccgcagggca gcgcgcggac     60
gacgggacca cggtgttccg gggcacggcg tactcgccgc tacggaccac ggtggcgctc    120
gcgctgtggc tcggggccat ccacttcaac gccttcctcg tcctcgcctc gctcttcctc    180
ttcccgcgcc gcgtcgccgc actggtgctg gcgacgcagc tcttcttcat gttcctgccg    240
ctcagtgata agagcagact gggccgcaag atcgccaggt tcataagcaa gtacgtcatt    300
gggtattttc ccgtcacttt gcacgtggaa gactatggcg cctttgatcc caacagggct    360
tatgtgttcg gttatgagcc tcattctgtt ttgcccatag ctgttgggat cctcggggac    420
cttgttggat tcatgccgct accaaagatg aagattcttg caagcagtgc ggtgttctac    480
accccgttcc taaggcaaat atggacatgg ttggggttgg ctcctgcgtc gagaaagagt    540
ttctactcct accttggagc tggttatagc tgtattatag tgccaggagg tgtgcaggaa    600
atacttcata tggatcatga ttcagaggtt gcttttctta aaccaagaaa aggttttgtt    660
aagatagcta ttgagatggg ttgccctgta gtccccgttt ttgctttcgg acagagctat    720
gtttacaaat ggtggaggcc aggtggcaag ttaattgtca agattgctag agcaatcaaa    780
ttttctccaa taatcttctg gggaaaactg gggactccca tcccttttgc aacaccaatg    840
catgtgattg ttgaaggcc aattgaggtt gtaaagaatc ctcaacctac cattgatgag    900
ataaaccaag tccacggaca gttcgttgtt gcgatgcaag atctgttcga gaatacaag    960

```
agcagaactg gataccctga tcttcagtta agagttcttt ga                    1002
```

<210> SEQ ID NO 20
<211> LENGTH: 333
<212> TYPE: PRT
<213> ORGANISM: Zea mays

<400> SEQUENCE: 20

```
Met Gly Ala Gly Thr Asn Asn Gly Leu Ser Asn Gly Ala Ala Gly
1               5                   10                  15

Gln Arg Ala Asp Asp Gly Thr Thr Val Phe Arg Gly Thr Ala Tyr Ser
            20                  25                  30

Pro Leu Arg Thr Thr Val Ala Leu Ala Leu Trp Leu Gly Ala Ile His
        35                  40                  45

Phe Asn Ala Phe Leu Val Leu Ala Ser Leu Phe Leu Phe Pro Arg Arg
    50                  55                  60

Val Ala Ala Leu Val Leu Ala Thr Gln Leu Phe Met Phe Leu Pro
65                  70                  75                  80

Leu Ser Asp Lys Ser Arg Leu Gly Arg Lys Ile Ala Arg Phe Ile Ser
                85                  90                  95

Lys Tyr Val Ile Gly Tyr Phe Pro Val Thr Leu His Val Glu Asp Tyr
            100                 105                 110

Gly Ala Phe Asp Pro Asn Arg Ala Tyr Val Phe Gly Tyr Glu Pro His
        115                 120                 125

Ser Val Leu Pro Ile Ala Val Gly Ile Leu Gly Asp Leu Val Gly Phe
    130                 135                 140

Met Pro Leu Pro Lys Met Lys Ile Leu Ala Ser Ser Ala Val Phe Tyr
145                 150                 155                 160

Thr Pro Phe Leu Arg Gln Ile Trp Thr Trp Leu Gly Leu Ala Pro Ala
                165                 170                 175

Ser Arg Lys Ser Phe Tyr Ser Tyr Leu Gly Ala Gly Tyr Ser Cys Ile
            180                 185                 190

Ile Val Pro Gly Gly Val Gln Glu Ile Leu His Met Asp His Asp Ser
        195                 200                 205

Glu Val Ala Phe Leu Lys Pro Arg Lys Gly Phe Val Lys Ile Ala Ile
    210                 215                 220

Glu Met Gly Cys Pro Val Val Pro Val Phe Ala Phe Gly Gln Ser Tyr
225                 230                 235                 240

Val Tyr Lys Trp Trp Arg Pro Gly Gly Lys Leu Ile Val Lys Ile Ala
                245                 250                 255

Arg Ala Ile Lys Phe Ser Pro Ile Ile Phe Trp Gly Lys Leu Gly Thr
            260                 265                 270

Pro Ile Pro Phe Ala Thr Pro Met His Val Ile Val Gly Arg Pro Ile
        275                 280                 285

Glu Val Val Lys Asn Pro Gln Pro Thr Ile Asp Glu Ile Asn Gln Val
    290                 295                 300

His Gly Gln Phe Val Val Ala Met Gln Asp Leu Phe Glu Lys Tyr Lys
305                 310                 315                 320

Ser Arg Thr Gly Tyr Pro Asp Leu Gln Leu Arg Val Leu
                325                 330
```

<210> SEQ ID NO 21
<211> LENGTH: 834
<212> TYPE: DNA
<213> ORGANISM: Glycine max -continued

```
<400> SEQUENCE: 21
atgcagacga aaaggatatt aaagtcattt tccagggtgt tcggtttgct cttggtgttc      60
gtgctcatcc tgtggacga aacagcatt tttggtcata aattgtccaa atacatatgc      120
aagcacattt gctcctattt tcccataacg cttcacgtag aagaagcaaa agcctttcgt    180
cctgatcaag cttatgtttt tgggtatgaa ccacactcgg ttttttccaat tggcattgtt    240
gcacttggtg acagcactgg cttcatgcct cttgcaaaaa caaaattct tgctagcagc     300
gccgtattct atataccatt tttgagacac atatggacat ggttaggatt tacgccagtg     360
acaaagcaaa atttcatttc ctcgttggaa gctggttaca gttgcatttt agtacctggt    420
ggagttcgag aaacattttt tatggagcct ggttgtgaga ttgcctttct taagcaaaga    480
agaggatttg tccgcatagc attgcaaatg ggcctacccc ttgttccagt tttctgcttt    540
ggccagacaa aagcctacaa gtggtggaag cctccaggaa ggttaatgca aaatcttgca    600
aggtttttga agataattcc attatttttc tggggtattt atggatctcc tataccattc    660
aaaaatccat tgtatatcgt cgtgggtaga ccaattgagc tagagaaaaa tccagaacca    720
acaatggagc aggttgccaa agtacatagt cagtttgttg aagcacttca agatctttttc    780
gaccgacaca agctcatgc tggatataca aatctcgagc tgaaaatatt ttga            834

<210> SEQ ID NO 22
<211> LENGTH: 277
<212> TYPE: PRT
<213> ORGANISM: Glycine max

<400> SEQUENCE: 22

Met Gln Thr Lys Arg Ile Leu Lys Ser Phe Ser Arg Val Phe Gly Leu
1               5                   10                  15

Leu Leu Val Phe Val Leu Ile Pro Val Asp Glu Asn Ser Ile Phe Gly
            20                  25                  30

His Lys Leu Ser Lys Tyr Ile Cys Lys His Ile Cys Ser Tyr Phe Pro
        35                  40                  45

Ile Thr Leu His Val Glu Glu Ala Lys Ala Phe Arg Pro Asp Gln Ala
    50                  55                  60

Tyr Val Phe Gly Tyr Glu Pro His Ser Val Phe Pro Ile Gly Ile Val
65                  70                  75                  80

Ala Leu Gly Asp Ser Thr Gly Phe Met Pro Leu Ala Lys Thr Lys Phe
                85                  90                  95

Leu Ala Ser Ser Ala Val Phe Tyr Ile Pro Phe Leu Arg His Ile Trp
            100                 105                 110

Thr Trp Leu Gly Phe Thr Pro Val Thr Lys Gln Asn Phe Ile Ser Ser
        115                 120                 125

Leu Glu Ala Gly Tyr Ser Cys Ile Leu Val Pro Gly Gly Val Arg Glu
    130                 135                 140

Thr Phe Phe Met Glu Pro Gly Cys Glu Ile Ala Phe Leu Lys Gln Arg
145                 150                 155                 160

Arg Gly Phe Val Arg Ile Ala Leu Gln Met Gly Leu Pro Leu Val Pro
                165                 170                 175

Val Phe Cys Phe Gly Gln Thr Lys Ala Tyr Lys Trp Trp Lys Pro Pro
            180                 185                 190

Gly Arg Leu Met Gln Asn Leu Ala Arg Phe Leu Lys Ile Ile Pro Leu
        195                 200                 205

Phe Phe Trp Gly Ile Tyr Gly Ser Pro Ile Pro Phe Lys Asn Pro Leu
```

```
             210                 215                 220
Tyr Ile Val Val Gly Arg Pro Ile Glu Leu Glu Lys Asn Pro Glu Pro
225                 230                 235                 240

Thr Met Glu Gln Val Ala Lys Val His Ser Gln Phe Val Glu Ala Leu
                245                 250                 255

Gln Asp Leu Phe Asp Arg His Lys Ala His Ala Gly Tyr Thr Asn Leu
            260                 265                 270

Glu Leu Lys Ile Phe
        275

<210> SEQ ID NO 23
<211> LENGTH: 999
<212> TYPE: DNA
<213> ORGANISM: Triticum aestivum

<400> SEQUENCE: 23
atgggcgcgg ggaatggcct gagcaacggc gccgcggccg cggccgaggc ggcgcccgac      60
gggaccacgg tgttccgggc cacggcctac tcgccgctgc gcaccacgct ggcgctggcg     120
ctctggctgg gggccatcca cttcaacatc tcctcgtcc tcgcctccct cttcctcctc     180
ccccgccgcg tcgccgccat ggtgctcggc acgcagctct tcttcatgct cgtgcccctc     240
aatgacagga gcaggatggg cgcaagatc gccagattca taagcaagta cgtgggggg      300 tacttccccg tcactctaca tgtggaggac tacaaggctg ttgaccccaa agagcttac     360 gtgttcggtt atgaaccgca ttctgttctg cccatcggcc ttggggccct cgtggacctt     420
gttggattca tgccattgcc gaagaccaag gttcttgcaa gcactgcggt gttctacact     480
ccgttcttga gcagatatg gacgtggttg gcttggttc ctgcttcaag aaagaacttc     540
tactcctacc ttcgagctgg ttatacctgc atcgtagtgc ctggaggtgt acaggagatg     600
cttcacatgg atcatgattc ggaggttgct tttctgaaat caaggaaagg ttttgttaag     660
atcgctatgg agacaggttc tcctttagtc ccggttttct gcttcggaca gagccttgtg     720
tacaagtggt ggaggccagg tggcaagttg attgtgaaga ttgctagagc aattaaattt     780
actccaatta ttttctttgg gaaatacggg actcccatcc ctttcgcgac accacttcat     840
ctggttgttg aagaccaat cgaggttcag aaaaatcctc agcctacata tgatgagata     900
aacgaggtac atgaacaatt tgtggttgcg atgcaagaac tattcgaaaa gtacaagaca     960
aaagctggat atgacaaact cgaattgaga gttctatga                            999

<210> SEQ ID NO 24
<211> LENGTH: 332
<212> TYPE: PRT
<213> ORGANISM: Triticum aestivum

<400> SEQUENCE: 24

Met Gly Ala Gly Asn Gly Leu Ser Asn Gly Ala Ala Ala Ala Glu
1               5                   10                  15

Ala Ala Pro Asp Gly Thr Thr Val Phe Arg Ala Thr Ala Tyr Ser Pro
            20                  25                  30

Leu Arg Thr Thr Leu Ala Leu Ala Leu Trp Leu Gly Ala Ile His Phe
        35                  40                  45

Asn Ile Leu Leu Val Leu Ala Ser Leu Phe Leu Leu Pro Arg Arg Val
    50                  55                  60

Ala Ala Met Val Leu Gly Thr Gln Leu Phe Phe Met Leu Val Pro Leu
65                  70                  75                  80
```

```
Asn Asp Arg Ser Arg Met Gly Arg Lys Ile Ala Arg Phe Ile Ser Lys
            85                  90                  95
Tyr Val Gly Gly Tyr Phe Pro Val Thr Leu His Val Glu Asp Tyr Lys
        100                 105                 110
Ala Val Asp Pro Lys Arg Ala Tyr Val Phe Gly Tyr Glu Pro His Ser
    115                 120                 125
Val Leu Pro Ile Gly Leu Gly Ala Leu Val Asp Leu Val Gly Phe Met
130                 135                 140
Pro Leu Pro Lys Thr Lys Val Leu Ala Ser Thr Ala Val Phe Tyr Thr
145                 150                 155                 160
Pro Phe Leu Arg Gln Ile Trp Thr Trp Leu Gly Leu Val Pro Ala Ser
                165                 170                 175
Arg Lys Asn Phe Tyr Ser Tyr Leu Arg Ala Gly Tyr Thr Cys Ile Val
            180                 185                 190
Val Pro Gly Gly Val Gln Glu Met Leu His Met Asp His Asp Ser Glu
        195                 200                 205
Val Ala Phe Leu Lys Ser Arg Lys Gly Phe Val Lys Ile Ala Met Glu
    210                 215                 220
Thr Gly Ser Pro Leu Val Pro Val Phe Cys Phe Gly Gln Ser Leu Val
225                 230                 235                 240
Tyr Lys Trp Trp Arg Pro Gly Gly Lys Leu Ile Val Lys Ile Ala Arg
                245                 250                 255
Ala Ile Lys Phe Thr Pro Ile Ile Phe Phe Gly Lys Tyr Gly Thr Pro
            260                 265                 270
Ile Pro Phe Ala Thr Pro Leu His Leu Val Val Gly Arg Pro Ile Glu
        275                 280                 285
Val Gln Lys Asn Pro Gln Pro Thr Tyr Asp Glu Ile Asn Glu Val His
    290                 295                 300
Glu Gln Phe Val Val Ala Met Gln Gly Leu Phe Glu Lys Tyr Lys Thr
305                 310                 315                 320
Lys Ala Gly Tyr Asp Lys Leu Glu Leu Arg Val Leu
                325                 330

<210> SEQ ID NO 25
<211> LENGTH: 1059
<212> TYPE: DNA
<213> ORGANISM: Drosophila melanogaster

<400> SEQUENCE: 25
atgaaaatcg agtgggcacc actgcgggtt cctctggaac gccgactgca gatactggtc      60
acggcctttt tcacctccat gctgctgata ctattgtcag tttccttcct tttggtagct     120
ggatcactga tctacggagg tcttttggtg cgtagtctga tggtaactta cttggcctac     180
gtctttgtgc accacaagaa aacccaatcc gttgtggatg gcaatggctg atgataaca      240
cgcaccaacc ttttgcatcg ccactatcgt gattacttc ccgtggagct ggtgaaaaca      300
gccgaactgc cagctactaa gaactacatc ttggccagct ttccccacgg aattctgggc     360
acaggcattg gcattaacat gggcttggaa atctccaagt ggctggagct attcccccaa     420
gtgcgtccca aactgggcac tctggatcag catttccatg ttccgttcat cgtgaggtc      480
ctccgctgct ggggtctggt gtcagtgtcc aaagaggcgc tgatccgtat gctcagcaag     540
tcaaatgatc ccaagcacaa ggataatcgg atggtttca cctccaatgc ggtggccatt      600
ctggttggcg gtgcccagga agccatggac tctcatcctg gcagtacat tttaaccttg      660
aagaatagga aaggcttcgt gcgaatggcc attagaacgg gctcatcgat tgttccttca     720
```

-continued

```
tttccttg gagaggtgga cattttcgat caggtggcaa atccccccaa ctcgctgctc    780
cgacggtttc aggactttgt caagaagctc accggagtct ctccgctgat tcctgtgggc    840
cgcggattct tcaactacac ctttggcttc ctcccattcc gacgacgcat tgtccaagtt    900
gttggtgctc ccatcgatgt tgttaagaac gagcacccag actcggagta tgtggataaa    960
gtgcatggac aggtcattga gtcgctggag aagttattcg atcagtacaa agacaagtac   1020
ttggagaatt cgaagagtgc cactctagtt gtacactag                          1059
```

<210> SEQ ID NO 26
<211> LENGTH: 352
<212> TYPE: PRT
<213> ORGANISM: Drosophila melanogaster

<400> SEQUENCE: 26

```
Met Lys Ile Glu Trp Ala Pro Leu Arg Val Pro Leu Glu Arg Arg Leu
 1               5                   10                  15

Gln Ile Leu Val Thr Ala Phe Phe Thr Ser Met Leu Leu Ile Leu Leu
                20                  25                  30

Ser Val Ser Phe Leu Leu Val Ala Gly Ser Leu Ile Tyr Gly Gly Leu
            35                  40                  45

Leu Val Arg Ser Leu Met Val Thr Tyr Leu Ala Tyr Val Phe Val His
        50                  55                  60

His Lys Lys Thr Gln Ser Val Val Asp Gly Asn Gly Trp Met Ile Thr
    65                  70                  75                  80

Arg Thr Asn Leu Leu His Arg His Tyr Arg Asp Tyr Phe Pro Val Glu
                85                  90                  95

Leu Val Lys Thr Ala Glu Leu Pro Ala Thr Lys Asn Tyr Ile Leu Ala
            100                 105                 110

Ser Phe Pro His Gly Ile Leu Gly Thr Gly Ile Gly Ile Asn Met Gly
        115                 120                 125

Leu Glu Ile Ser Lys Trp Leu Glu Leu Phe Pro Gln Val Arg Pro Lys
    130                 135                 140

Leu Gly Thr Leu Asp Gln His Phe His Val Pro Phe Met Arg Glu Val
145                 150                 155                 160

Leu Arg Cys Trp Gly Leu Val Ser Val Ser Lys Glu Ala Leu Ile Arg
                165                 170                 175

Met Leu Ser Lys Ser Asn Asp Pro Lys His Lys Asp Asn Arg Asp Gly
            180                 185                 190

Phe Thr Ser Asn Ala Val Ala Ile Leu Val Gly Gly Ala Gln Glu Ala
        195                 200                 205

Met Asp Ser His Pro Gly Gln Tyr Ile Leu Thr Leu Lys Asn Arg Lys
    210                 215                 220

Gly Phe Val Arg Met Ala Ile Arg Thr Gly Ser Ser Ile Val Pro Ser
225                 230                 235                 240

Phe Ser Phe Gly Glu Val Asp Ile Phe Asp Gln Val Ala Asn Pro Pro
                245                 250                 255

Asn Ser Leu Leu Arg Arg Phe Gln Asp Phe Val Lys Lys Leu Thr Gly
            260                 265                 270

Val Ser Pro Leu Ile Pro Val Gly Arg Gly Phe Phe Asn Tyr Thr Phe
        275                 280                 285

Gly Phe Leu Pro Phe Arg Arg Arg Ile Val Gln Val Val Gly Ala Pro
    290                 295                 300

Ile Asp Val Val Lys Asn Glu His Pro Asp Ser Glu Tyr Val Asp Lys
```

```
             305                 310                 315                 320
Val His Gly Gln Val Ile Glu Ser Leu Glu Lys Leu Phe Asp Gln Tyr
                325                 330                 335

Lys Asp Lys Tyr Leu Glu Asn Ser Lys Ser Ala Thr Leu Val Val His
                340                 345                 350

<210> SEQ ID NO 27
<211> LENGTH: 1005
<212> TYPE: DNA
<213> ORGANISM: Homo sapiens

<400> SEQUENCE: 27
atgaaggtag agtttgcacc gctcaacatc cagctggcgc ggcggctgca gacggtggcc      60
gtgctgcagt gggtcctttc ttttcttaca gggccgatgt ccattggaat cactgtgatg     120
ctgatcatac acaactattt gttcctttac atcccttatt tgatgtggct ttactttgac     180
tggcataccc cagagcgagg aggcaggaga tccagctgga tcaaaaattg gactctttgg     240
aaacacttta aggactattt tccaattcat cttatcaaaa ctcaagattt ggatccaagt     300
cacaactata tatttgggtt tcaccccat ggaataatgg cagttggagc ctttgggaat     360
ttttctgtaa attattctga cttcaaggac ctgtttcctg ctttacttc atatcttcac     420
gtgctgccac tttggttctg gtgtcctgtc tttcgagaat atgtgatgag tgttgggctg     480
gtttcagttt ccaagaaaag tgtgtcctac atggtaagca aggagggagg tggaaacatc     540
tctgtcattg tccttggggg tgcaaaagaa tcactggatg ctcatcctgg aaagttcact     600
ctgttcatcc gccagcggaa aggatttgtt aaaattgctt tgacccatgg cgcctctctg     660
gtcccagtgg tttcttttgg tgaaaatgaa ctgtttaaac aaactgacaa ccctgaagga     720
tcatggatta gaactgttca gaataaactg cagaagatca tggggtttgc tttgccctg      780
tttcatgcca ggggagtttt tcagtacaat tttggcctaa tgacctatag gaaagccatc     840
cacactgttg ttggccgccc gatccctgtt cgtcagactc tgaacccgac ccaggagcag     900
attgaggagt acatcagac ctatatggag gaacttagga aattgtttga ggaacacaaa     960
ggaaagtatg gcattccaga gcacgagact cttgttttaa aatga                    1005

<210> SEQ ID NO 28
<211> LENGTH: 334
<212> TYPE: PRT
<213> ORGANISM: Homo sapiens

<400> SEQUENCE: 28

Met Lys Val Glu Phe Ala Pro Leu Asn Ile Gln Leu Ala Arg Arg Leu
1               5                   10                  15

Gln Thr Val Ala Val Leu Gln Trp Val Leu Ser Phe Leu Thr Gly Pro
                20                  25                  30

Met Ser Ile Gly Ile Thr Val Met Leu Ile Ile His Asn Tyr Leu Phe
            35                  40                  45

Leu Tyr Ile Pro Tyr Leu Met Trp Leu Tyr Phe Asp Trp His Thr Pro
        50                  55                  60

Glu Arg Gly Gly Arg Arg Ser Ser Trp Ile Lys Asn Trp Thr Leu Trp
65                  70                  75                  80

Lys His Phe Lys Asp Tyr Phe Pro Ile His Leu Ile Lys Thr Gln Asp
                85                  90                  95

Leu Asp Pro Ser His Asn Tyr Ile Phe Gly Phe His Pro His Gly Ile
            100                 105                 110
```

```
Met Ala Val Gly Ala Phe Gly Asn Phe Ser Val Asn Tyr Ser Asp Phe
            115                 120                 125

Lys Asp Leu Phe Pro Gly Phe Thr Ser Tyr Leu His Val Leu Pro Leu
    130                 135                 140

Trp Phe Trp Cys Pro Val Phe Arg Glu Tyr Val Met Ser Val Gly Leu
145                 150                 155                 160

Val Ser Val Ser Lys Lys Ser Val Ser Tyr Met Val Ser Lys Glu Gly
                165                 170                 175

Gly Gly Asn Ile Ser Val Ile Val Leu Gly Gly Ala Lys Glu Ser Leu
            180                 185                 190

Asp Ala His Pro Gly Lys Phe Thr Leu Phe Ile Arg Gln Arg Lys Gly
            195                 200                 205

Phe Val Lys Ile Ala Leu Thr His Gly Ala Ser Leu Val Pro Val Val
            210                 215                 220

Ser Phe Gly Glu Asn Glu Leu Phe Lys Gln Thr Asp Asn Pro Glu Gly
225                 230                 235                 240

Ser Trp Ile Arg Thr Val Gln Asn Lys Leu Gln Lys Ile Met Gly Phe
                245                 250                 255

Ala Leu Pro Leu Phe His Ala Arg Gly Val Phe Gln Tyr Asn Phe Gly
            260                 265                 270

Leu Met Thr Tyr Arg Lys Ala Ile His Thr Val Val Gly Arg Pro Ile
            275                 280                 285

Pro Val Arg Gln Thr Leu Asn Pro Thr Gln Glu Gln Ile Glu Glu Leu
            290                 295                 300

His Gln Thr Tyr Met Glu Glu Leu Arg Lys Leu Phe Glu Glu His Lys
305                 310                 315                 320

Gly Lys Tyr Gly Ile Pro Glu His Glu Thr Leu Val Leu Lys
                325                 330

<210> SEQ ID NO 29
<211> LENGTH: 346
<212> TYPE: PRT
<213> ORGANISM: Schizosaccharomyces pombe
<220> FEATURE:
<221> NAME/KEY: MISC_FEATURE
<222> LOCATION: (1)..(346)
<223> OTHER INFORMATION: any set containing n

<400> SEQUENCE: 29

Met Ser Glu Glu Thr Ser Ile Pro Gly Ile Ile Ala Ser Thr Pro Pro
1               5                   10                  15

Ile Ser Lys Asp Ser Arg Arg Asn Val Ser His Trp Leu Gln Ala Leu
            20                  25                  30

Ala Val Phe Leu His Ser Val Ser Leu Thr Leu Thr Ala Ser Trp Tyr
        35                  40                  45

Thr Val Leu Trp Ala Phe Leu Pro Phe Trp Pro Val Ser Glu His Leu
    50                  55                  60

Phe Xaa Cys Tyr Asn Ile Asn Asp Phe Xaa Lys Xaa Asn Phe Ile Cys
65                  70                  75                  80

Lys Met Tyr Arg Asp Ser Asn Cys Xaa Lys Lys Ala Leu Gly Ile Ser
            85                  90                  95

Cys Leu Phe Asp Asp Thr Lys Tyr Phe Ser Val Phe Gly Leu Gln Lys
            100                 105                 110

Xaa Ser Val Ser Leu Pro Phe Leu Lys Cys Xaa Lys Leu Ile His Leu
        115                 120                 125

Phe Phe Phe Thr Val His Phe Thr Asn Pro Ser Phe Leu Xaa Phe Leu
```

```
                130                 135                 140
Ile Val Tyr Leu Ile Trp Leu Ile Tyr Asp Asp Gly Phe Val Thr Gly
145                 150                 155                 160

Lys Asp Arg Gln Lys Arg Trp Leu Arg Asn Ala Pro Pro Tyr Arg Trp
                165                 170                 175

Phe Cys His Tyr Phe Pro Ile Arg Leu His Lys Thr Thr Glu Leu Asp
            180                 185                 190

Ser Glu Lys Asn Tyr Ile Phe Gly Tyr His Pro His Gly Ile Ile Ser
            195                 200                 205

Leu Gly Ala Phe Gly Gly Phe Ala Ser Glu Gly Met Leu Xaa Trp Arg
210                 215                 220

Thr Arg Lys Leu Glu Ala Thr Leu His Gln Cys Phe Pro Phe Xaa Phe
225                 230                 235                 240

His Thr Xaa Phe Ser Tyr Leu Ile Ser Asn Leu Met Leu Leu Gly Ala
            245                 250                 255

Asp Phe Ser Lys Leu Phe Pro Gly Ile Asn Val Ser Val Leu Thr Leu
            260                 265                 270

Asn Ser Asn Phe Tyr Val Pro Val Tyr Arg Asp Tyr Leu Met Ala Leu
            275                 280                 285

Asn Ile Asn Ser Val Ser Lys Lys Ser Cys Val Ser Ile Leu Ser Arg
290                 295                 300

Lys Pro Gly Asp Ser Val Leu Ile Val Ile Gly Gly Ala Gln Glu Ser
305                 310                 315                 320

Leu Leu Ser Arg Pro Gly Gln Asn Asn Leu Val Leu Lys Lys Arg Phe
                325                 330                 335

Gly Phe Val Lys Leu Ala Phe Leu Thr Gly
            340                 345

<210> SEQ ID NO 30
<211> LENGTH: 228
<212> TYPE: PRT
<213> ORGANISM: Schizosaccharomyces pombe

<400> SEQUENCE: 30

Met Ser Glu Glu Thr Ser Ile Pro Gly Ile Ile Ala Ser Thr Pro Pro
1               5                   10                  15

Ile Ser Lys Asp Ser Arg Arg Asn Val Ser His Trp Leu Gln Ala Leu
                20                  25                  30

Ala Val Phe Leu His Ser Val Ser Leu Thr Leu Thr Ala Ser Trp Tyr
            35                  40                  45

Thr Val Leu Trp Ala Phe Leu Pro Phe Trp Pro Phe Leu Ile Val Tyr
        50                  55                  60

Leu Ile Trp Leu Ile Tyr Asp Asp Gly Phe Val Thr Gly Lys Asp Arg
65                  70                  75                  80

Gln Lys Arg Trp Leu Arg Asn Ala Pro Pro Tyr Arg Trp Phe Cys His
                85                  90                  95

Tyr Phe Pro Ile Arg Leu His Lys Thr Thr Glu Leu Asp Ser Glu Lys
            100                 105                 110

Asn Tyr Ile Phe Gly Tyr His Pro His Gly Ile Ile Ser Leu Gly Ala
            115                 120                 125

Phe Gly Gly Phe Ala Ser Glu Gly Ala Asp Phe Ser Lys Leu Phe Pro
        130                 135                 140

Gly Ile Asn Val Ser Val Leu Thr Leu Asn Ser Asn Phe Tyr Val Pro
145                 150                 155                 160
```

-continued

```
Val Tyr Arg Asp Tyr Leu Met Ala Leu Asn Ile Asn Ser Val Ser Lys
                165                 170                 175

Lys Ser Cys Val Ser Ile Leu Ser Arg Lys Pro Gly Asp Ser Val Leu
            180                 185                 190

Ile Val Ile Gly Gly Ala Gln Glu Ser Leu Leu Ser Arg Pro Gly Gln
        195                 200                 205

Asn Asn Leu Val Leu Lys Lys Arg Phe Gly Phe Val Lys Leu Ala Phe
    210                 215                 220

Leu Thr Gly Ser
225

<210> SEQ ID NO 31
<211> LENGTH: 577
<212> TYPE: PRT
<213> ORGANISM: Candida albicans

<400> SEQUENCE: 31

Met Thr Asp Thr Ser Asp Leu Lys Pro Glu His Thr Glu Lys Ala Thr
1               5                   10                  15

Gly Leu Ser Thr Ser Lys Glu Val Pro Glu Ser Thr Leu Thr Gln Arg
            20                  25                  30

Lys Gln Pro Ser Thr Pro Ala Thr Gln Thr Ser Lys Arg Pro Thr Pro
        35                  40                  45

Ala Lys Lys Lys Arg Ala Phe Ile Asn Val Ala Pro Leu Asn Thr Pro
    50                  55                  60

Leu Ser His Arg Leu Glu Thr Leu Gly Val Val Trp His Cys Ile Ser
65                  70                  75                  80

Ile Pro Phe Phe Ile Cys Leu Phe Phe Met Ile Ser Leu Gly Leu
                85                  90                  95

Phe Gly Trp Ile Val Ile Val Leu Pro Tyr Phe Ile Trp Trp Tyr Gly
            100                 105                 110

Phe Asp Leu His Thr Pro Thr Asn Gly Lys Val Ala Tyr Arg Tyr Arg
        115                 120                 125

Asn Ser Met Lys Asn Phe Ile Ile Trp Asp Trp Phe Val Arg Tyr Phe
    130                 135                 140

Pro Ile Lys Val Tyr Lys Ser Val Glu Leu Glu Pro Thr Phe Lys Glu
145                 150                 155                 160

Val Leu Val Glu Glu Thr Glu Ser Ser Glu Asp Asp Glu Gln Asp
                165                 170                 175

Leu Val Ser Glu Arg Ser Arg Thr Leu Val Asp Lys Val Phe Lys Phe
            180                 185                 190

Phe Gly Leu Lys Lys Arg Leu Asn Asp Thr Ser Leu Gly Lys Ser Glu
        195                 200                 205

Thr Tyr Lys Thr Val Ser Thr Gly Pro Arg Tyr Ile Phe Gly Tyr His
    210                 215                 220

Pro His Gly Val Ile Ser Met Gly Gly Val Gly Leu Phe Ala Thr Asn
225                 230                 235                 240

Ser Leu Arg Asn Glu Pro Tyr Thr Pro Phe Leu Lys Phe Leu Lys Pro
                245                 250                 255

Phe Phe His Asp Ser Ser Lys Gly Glu Arg Leu Phe Pro Gly Leu Gly
            260                 265                 270

Asn Ile Phe Leu Leu Thr Ile Thr Thr Gln Phe Ala Ile Pro Phe Tyr
        275                 280                 285

Arg Asp Tyr Leu Met Gly Leu Gly Val Thr Ser Ala Ser Ala Lys Asn
    290                 295                 300
```

```
Ile Arg Ser Leu Ile Ser Asn Gly Asp Asn Ser Val Cys Ile Val Val
305                 310                 315                 320

Gly Gly Ala Glu Glu Ser Leu Leu Asn Asn Met Val Ala Lys His Ala
            325                 330                 335

Arg Val Gly Tyr Gly Tyr Lys Glu Asn Gln Asp Ile Asn Gly Ser Asp
            340                 345                 350

Ala Glu Asp Asp Gln Pro Glu Glu Glu Gln Gln Gln Gln Gln Gln Gln
        355                 360                 365

Pro Asn Gly Ser Val Glu Val Asp Lys Lys Thr Thr Lys Glu Val Gly
370                 375                 380

Glu Lys Thr Ser Ser Gln Pro Ser Lys Arg Glu Val Lys Leu Ile Leu
385                 390                 395                 400

Asn Lys Arg Lys Gly Phe Val Lys Leu Ala Ile Glu Leu Gly Asn Val
            405                 410                 415

Ala Leu Val Pro Thr Phe Ala Phe Gly Glu Ala Asp Val Tyr Arg Leu
            420                 425                 430

Val Gln Pro Ser Pro Thr Ser Met Met Tyr Lys Phe Gln Lys Trp Met
        435                 440                 445

Lys Gly Ile Phe Leu Phe Thr Ile Pro Leu Phe Ser Ala Arg Gly Val
450                 455                 460

Phe Ile Tyr Asp Tyr Gly Leu Leu Pro Phe Arg Asn Pro Ile Asn Ile
465                 470                 475                 480

Cys Val Gly Lys Pro Ile Tyr Ile Pro Ala Gly Ala Leu Gln Glu Tyr
            485                 490                 495

Lys Gln Gln His Pro Glu Glu Phe Thr Glu Glu Thr Lys Pro Pro
        500                 505                 510

Met Lys Lys Ser Gly Ser Phe Thr Asp Ile Phe Lys Met Asn Gly Glu
            515                 520                 525

Thr Pro Lys Val Ser Thr Ile Lys Thr Lys Ile Pro Pro Ala Leu Leu
        530                 535                 540

Asp Lys Tyr His Lys Leu Tyr Val Asp Glu Leu Arg Asn Val Tyr Glu
545                 550                 555                 560

Glu Asn Lys His Lys Phe Gly Tyr Gly Asp Val Glu Phe Ser Ile Val
                565                 570                 575

Glu

<210> SEQ ID NO 32
<211> LENGTH: 314
<212> TYPE: PRT
<213> ORGANISM: Arabidopsis thaliana

<400> SEQUENCE: 32

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65              70                  75                  80

Ala Cys Asn Tyr Phe Pro Val Ser Leu Tyr Val Glu Asp Tyr Glu Ala
                85                  90                  95
```

```
Phe Gln Pro Asn Arg Ala Tyr Val Phe Gly Tyr Glu Pro His Ser Val
                100                 105                 110
Leu Pro Ile Gly Val Val Ala Leu Cys Asp Leu Thr Gly Phe Met Pro
            115                 120                 125
Ile Pro Asn Ile Lys Val Leu Ala Ser Ser Ala Ile Phe Tyr Thr Pro
        130                 135                 140
Phe Leu Arg His Ile Trp Thr Trp Leu Gly Leu Thr Ala Ala Ser Arg
145                 150                 155                 160
Lys Asn Phe Thr Ser Leu Leu Asp Ser Gly Tyr Ser Cys Val Leu Val
                165                 170                 175
Pro Gly Gly Val Gln Glu Thr Phe His Met Gln His Asp Ala Glu Asn
            180                 185                 190
Val Phe Leu Ser Arg Arg Gly Phe Val Arg Ile Ala Met Glu Gln
        195                 200                 205
Gly Ser Pro Leu Val Pro Val Phe Cys Phe Gly Gln Ala Arg Val Tyr
            210                 215                 220
Lys Trp Trp Lys Pro Asp Cys Asp Leu Tyr Leu Lys Leu Ser Arg Ala
225                 230                 235                 240
Ile Arg Phe Thr Pro Ile Cys Phe Trp Gly Val Phe Gly Ser Pro Leu
                245                 250                 255
Pro Cys Arg Gln Pro Met His Val Val Val Gly Lys Pro Ile Glu Val
            260                 265                 270
Thr Lys Thr Leu Glu Pro Thr Asp Glu Ile Ala Lys Phe His Gly
        275                 280                 285
Gln Tyr Val Glu Ala Leu Arg Asp Leu Phe Glu Arg His Lys Ser Arg
            290                 295                 300
Val Gly Tyr Asp Leu Glu Leu Lys Ile Leu
305                 310

<210> SEQ ID NO 33
<211> LENGTH: 14
<212> TYPE: PRT
<213> ORGANISM: Artificial
<220> FEATURE:
<221> NAME/KEY: MISC_FEATURE
<222> LOCATION: (1)..(12)
<223> OTHER INFORMATION: Xaa is any amino acid

<400> SEQUENCE: 33

Ala Tyr Val Phe Gly Tyr Glu Pro His Ser Val Xaa Pro Ile
1               5                   10

<210> SEQ ID NO 34
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(7)
<223> OTHER INFORMATION: Xaa is any amino acid

<400> SEQUENCE: 34

Phe Xaa Xaa Pro Xaa Tyr Arg
1               5
```